US006570040B2

(12) United States Patent
Saxon et al.

(10) Patent No.: US 6,570,040 B2
(45) Date of Patent: May 27, 2003

(54) CHEMOSELECTIVE LIGATION

(75) Inventors: Eliana Saxon, Albany, CA (US); Carolyn Bertozzi, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/810,864

(22) Filed: Mar. 16, 2001

(65) Prior Publication Data
US 2002/0016003 A1 Feb. 7, 2002

Related U.S. Application Data
(60) Provisional application No. 60/189,837, filed on Mar. 16, 2000.
(51) Int. Cl.[7] .............................. C12N 5/02; C12P 7/40; B01J 31/00; C07F 9/02; C07C 67/38
(52) U.S. Cl. .................... 568/17; 435/136; 435/325; 502/162; 560/233; 568/7; 568/8
(58) Field of Search ................. 435/136, 325; 502/162; 560/233; 568/7, 8, 17

(56) References Cited

U.S. PATENT DOCUMENTS 4,292,437 A * 9/1981 Squire et al.

FOREIGN PATENT DOCUMENTS

| WO | WO 89/08657 | 9/1989 |
| WO | WO 01/87920 | 11/2001 |

OTHER PUBLICATIONS

Ravindar et al. 1992, Synth. Comm., 22, 1453–1459, 1992.*
Chatt et al. (1973) Rhodium(I), Rhodium(III), Palladium(II), and Platinum(II) complexes containing Ligands of the TypePR"Q$_{3-n}$(n=0,1,or2; R= Me, Et, Bu, or Ph; Q=CH$_2$OCOMe or Ch$_2$OH). Journal of Chemical Society No. 19 pp. 2021–2028.
Markl et al (1980) 1,5–Diaza–3–phopha–cyclohepatne–N, N'–Bis–'[phosphinomethyl]–Ethylendiamine MIT Optisch Aktiven Seitenketten, Tetrahedron Letters vol. 21 pp. 3467–3470.
Saxon et al. (Mar. 17, 2000) Cell Surface Engineering by a Modified Staudinger Reaction. Science vol. 287 No. 5460 pp. 2007–2010.
Saxon et al.(1999) Development of a New Chemoselective Ligation Reaction, Abstracts of Papers American Chemical Society vol. 218 No. 1–2 PP. Carb 23.
Kiick et al. (2000) "Protein Engineering by In Vivo Incorporation of Non–Natural Amino Acids Control of Incorporation of Methionine Analogues by Methionyl–tRNA Synthetase." Tetrahedron, vol. 56:9487–9493.
Kosa et al. (1993) "Modification of Cell Surfaces by Enzymatic Introduction of Special Sialic Acid Analogues." Biochemical and Biophysical Research Communications, vol. 190(3):914–921.

Lee et al. (1999) "Engineering Novel Cell Surface Receptors for Virus–mediated Gene Transfer." The Journal of Biological Chemistry, vol. 274(31):21878–21884.
Leffler et al. (1967) "The Staudinger Reaction between Triarylphosphines and Azides. A Study of the Mechanism." J. Am. Chem. Soc., vol. 89:5235–5246.
Lemieux et al. (1998) "Chemoselective ligation reactions with proteins, oligosaccharides and cells." Trends Biotechnol., vol. 16:506–513.
Lemieux et al. (1999) "Exploiting Differences in Sialoside Expression for Selective Targeting of MRI Contrast Reagents." J. Am. Chem. Soc., vol. 121:4278–4279.
Mahal et al. (1997) "Engineering Chemical Reactivity on Cell Surfaces through Oligosaccharide biosynthesis." Science, vol. 276:1125–1128.
Marcaurelle et al. (1998) "Direct Incorporation of Unprotected Ketone Groups into Peptides During Solid–Phase Syntheiss: Application to the One–Step Modification of Peptides with Two Different Biophysical Probes for FRET." Tetrahedron Letters, vol. 39:7279–7282.
Marcaurelle et al. (1998) "Synthesis of an Oxime–Linked Neoglycopeptide with Glycosylation–dependent Activity similar to its Native Counterpart." Tetrahedron Letters, vol. 39:8417–8420.
Mastryukova et al. (1989) "Amide–Imide Rearrangement in β–Chloroethyl Esters of Phosphorus Acid N–Phenylimides." Zh. Obshch. Khim., vol. 58(9):1967–1973.
Rodriguez et al. (1998) "Aminooxy–, Hydrazide–, and Thiosemicarbazide–Functionalized Saccharides: Versatile Reagents for Glycoconjugate Synthesis." J. Org. Chem., vol. 63:7134–7135.
Sarkar et al. (1995) "Disaccharide uptake and priming in animal cells: Inhibition of sialyl Lewis X by acetylated Galβ1→4GlcNAcβ–O–naphthalenemethanol." Proc. Natl. Acad. Sci. USA, vol. 92:3323–3327.
Slany et al. (1996) "Specific Functionalization on the Surface of Dendrimers." Tetrahedron Letters, vol. 37(50):9053–9056.

(List continued on next page.)

Primary Examiner—Leon B. Lankford, Jr.
Assistant Examiner—Kailash C. Srivastava
(74) Attorney, Agent, or Firm—Paula A. Bordan; Carol L. Francis; Boziecevic, Field & Francis, LLP

(57) ABSTRACT

The present invention features a chemoselective ligation reaction that can be carried out under physiological conditions. In general, the invention involves condensation of a specifically engineered phosphine, which can provide for formation of an amide bond between the two reactive partners resulting in a final product comprising a phosphine moiety, or which can be engineered to comprise a cleavable linker so that a substituent of the phosphine is transferred to the azide, releasing an oxidized phosphine byproduct and producing a native amide bond in the final product. The selectivity of the reaction and its compatibility with aqueous environments provides for its application in vivo (e.g., on the cell surface or intracellularly) and in vitro (e.g., synthesis of peptides and other polymers, production of modified (e.g., labeled) amino acids).

4 Claims, 10 Drawing Sheets

OTHER PUBLICATIONS

Souers et al. (1999) "Preparation of Enantioenriched α–Bromo Acids Incorporating Diverse Functionality." *Synthesis–Stuttgart,* vol. 4:583–585.

Staudinger et al. (1919) "Über neue organische Phosphorverbindunge III. Phosphinmethylenderivate und Phosphinime." *Helv. Chim. Acta.,* vol. 2:635–646.

Wilt et al. (1985) "A New synthesis of Peptides from Azides and Unactivated Carboxylic Acids." *J. Org. Chem.,* vol. 50:2601–2603.

Winans et al. (1998) "Inner space exploration: the chemical biologist's guide to the cell." *Chemistry & Biology,* vol. 5:R313–R315.

Yarema et al. (1998) "Metabolic Delivery of Ketone Groups to Sialic Acid Residues." *The Journal of Biological Chemistry,* vol. 273(47):31168–31179.

* cited by examiner

ManLev inhibition by ManAzide

Scheme 9a

Scheme 9b

Scheme 17

CHEMOSELECTIVE LIGATION

CROSS-REFERENCE TO RELATED APPLICATIONS

This application claims the benefit of U.S. Provisional Application Serial No. 60/189,837, filed Mar. 16, 2000, which application is incorporated herein by reference in its entirety.

STATEMENT AS TO FEDERALLY SPONSORED RESEARCH

This invention was made, at least in part, with a government grant from the National Institutes of Health (Grant Nos. NIH grant GM58867-01), the Office of Naval Research (Grant No. N00014-98-0605), and the Department of Energy (Order No. N00014-98-F-0402, Contract No. DE-AC03-76SF00098). The U.S. government may have certain rights in this invention.

FIELD OF THE INVENTION

The invention relates generally to covalent modification of molecules useful in, for example, construction of chemical libraries (including peptide libraries,), modification of surfaces (including cell surfaces), and modification of molecules under physiological conditions (e.g., in a cellular environment).

BACKGROUND OF THE INVENTION

Nature executes a remarkable feat of achieving molecular recognition in the complex environment of the cellular world. Antibodies bind a single antigen with high affinity, enzymes act on specific substrates in the presence of an enormous variety of similar compounds, and signaling molecules only trigger responses in their target cells. Recently, chemists have attempted to mimic this selectivity by developing a repertoire of reactions that can take place in the presence of other functional groups, and ultimately within the medium of a living cell. Ideally, the reactive partners would be abiotic, react rapidly in water at physiological pH and temperature, form a stable adduct under physiological conditions, and recognize only each other while ignoring their cellular surroundings. The demands on selectivity imposed by cells preclude the use of most conventional covalent reactions. Given these constraints and demands it is not surprising that only a handful of such reactions exist.

When the reaction results in coupling of the two reactants it is termed a "chemoselective ligation" (Lemieux et al. *Trends Biotechnol.* 1998, 16, 506). First described in the arena of protein chemistry, the term is used to describe the coupling of two functional groups in an aqueous environment. The coupling partners are mutually and uniquely reactive, thereby eliminating the need for protecting groups on surrounding functional groups. Chemoselective ligation reactions have been designed for modification of cell surfaces, as well as to provide for ligation reactions in peptide synthesis. Chemoselective ligation reactions have also been designed to modify only one cellular component among all others have provided unique insight into cellular processes (Winans et al. *Chem. Biol.* 1998, 5, R313).

Three common examples of chemoselective ligation reactions are shown below in Table 1 (Lemieux et al. *Trends Biotechnol.* 1998, 16, 506). These electrophile-nucleophile pairs have orthogonal reactivity to other functional groups present in many biomolecules.

TABLE 1

Chemoselective ligation reactions.

| Chemoselective coupling partners | Product |
|---|---|
| Aldehyde: R' = H; Ketone: R' = alkyl  +  Hydrazide | Hydrazone |
| R(C=O)R' + H₂N—OR'' (Aminooxy) | Oxime |
| Thiocarboxylate + α-Halo carbonyl | Thioester |

The chemoselective ligation reaction between a ketone and an aminooooxy or hydrazide group has enabled the engineering of the composition of cell surfaces, and has been used for both in vitro and in vivo chemoselective ligations. Mahal et al. *Science* 1997, 276, 1125; Brownlee et al. *Science* 1986, 232, 1629. While not entirely abiotic, the ketone is generally orthogonal to the reactivity of the functional groups present in the outer coating of the cell, which is composed of a variety of heterogeneous glycoproteins) Gumbiner *Cell* 1996, 84, 345. In vivo chemoselective ligation on the cell surface can be accomplished through unnatural sialic acid biosynthesis. (Kayser et al. *J. Biol. Chem.* 1992, 267, 16934; Kosa et al. *Biochem. Biophys. Res. Comm.* 1993, 190, 914; Keppler et al. *J. Biol. Chem.* 1995, 270, 1308).

Human cells metabolize the unnatural precursor N-levulinoylmannosamine (ManLev, 3 below), a ketone-bearing analog of the native sugar N-acetylmannosamine (1). The substrate promiscuity of this pathway permits the metabolism of the unnatural ManLev precursor 3 into sialic acid analogs 4 on living cells, resulting in the display of ketones (shown as boxes in the schematic below) on the cell surface. These metabolically installed ketones give the cell a unique reactivity, thereby allowing modification of cell surfaces by chemoselective ligation with any moiety bearing a hydrazide or aminooxy group. (Mahal et al. *Science* 1997, 276, 1125). The ability to perform orthogonal chemical reactions on cell surfaces has enabled the decoration of cells with synthetic glycans (Yarema et al. *J. Biol. Chem.* 1998, 273, 31168), targeting of MRI probes to tumor cells (Lemieux et al. *J. Am. Chem. Soc.* 1999, 121, 4278), and production of novel receptors for facilitating viral-mediated gene transfer (Lee et al. *J. Biol. Chem.* 1999, 274, 21878).

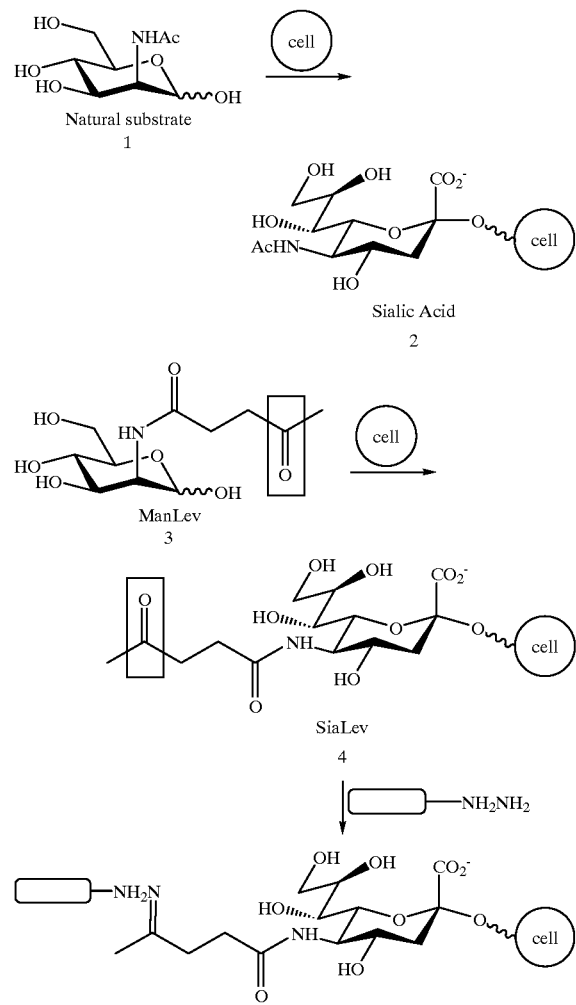

While useful for cell surface chemistry, ketone ligation reactions have limited intracellular utility due to competition with endogenous keto-metabolites. Tsien and coworkers reported a second chemoselective ligation reaction that circumvents this problem by providing for condensation of a unique cysteine-rich hexapeptide motif with a bis-dithioarsolane (Griffin et al. *Science* 1998, 281, 269). This enabled the targeting of a synthetic fluorescent dye to a single protein within the environs of a living cell.

In addition to its usefulness for modification of cell surfaces, the unique reactivity of the ketone has also been exploited for glycopeptide synthesis. Ketone-bearing amino acids have been incorporated into a synthetic peptide, allowing subsequent chemoselective ligation. This method was used to glycosylate synthetic peptides at defined locations via an unnatural oxime linkage (illustrated in the schematic below), enabling the synthesis of otherwise intractable glycoproteins and permitting the investigation of the effect of glycosylation on protein structure and function (Marcaurelle et al. *Tetrahedron Lett.* 1998, 39, 8417); (Marcaurelle et al. *Tetrahedron Lett.* 1998, 39, 7279); (Rodriguez et al. *J. Org. Chem.* 1998, 63, 7134).

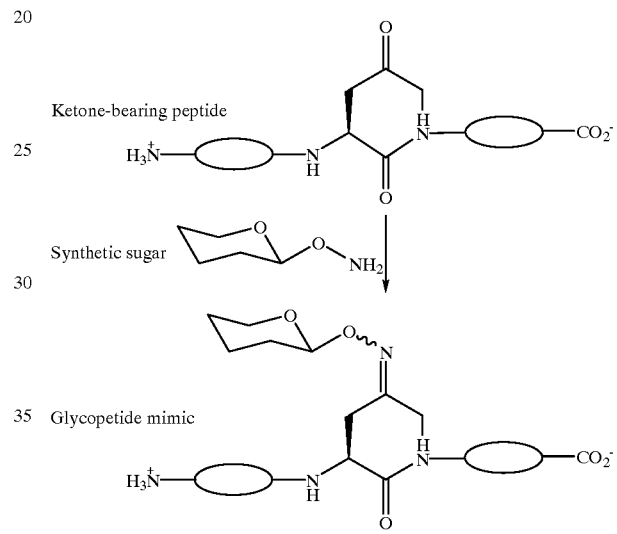

A subset of chemoselective ligations results in the formation of a native bond within a peptide. Kent and coworkers developed such a method, termed native chemical ligation, for the construction of large proteins that are far beyond the realm of stepwise solid phase peptide synthesis. (Canne et al. *J. Am. Chem. Soc.* 1996, 118, 5891). The reaction exploits a selective trans-thioesterification (as depicted in the reaction below). One peptide segment bearing a C-terminal thioester reacts with another bearing an N-terminal cysteine residue. The fast initial step is followed by a spontaneous irreversible rearrangement to form a native peptide bond. This methodology has been exploited for the synthesis of proteins containing suitably positioned cysteine residues. (Dawson et al. *Science* 1994, 266, 776).

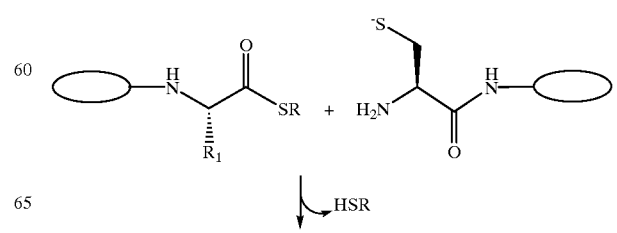

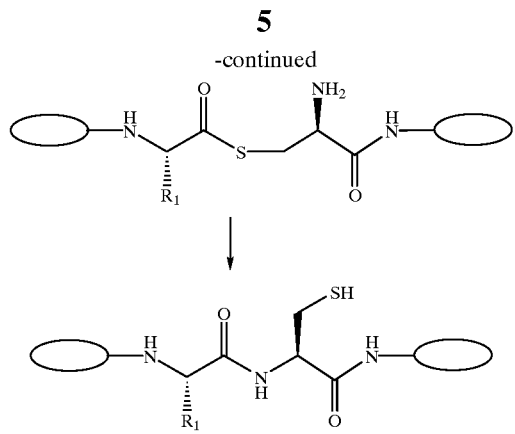

The addition of new chemoselective reactions to the rather limited existing panel would expand the utility of this chemistry and enable novel applications. For example, the cell surface display of two different, orthogonally reactive functional groups would allow the tandem delivery of biological probes, drugs or homogeneous carbohydrate moieties in a chemically controlled manner. Furthermore, an entirely abiotic functional group could be used to form covalent adducts within a cell, thus providing a unique target for modification. In addition, a novel reactive pair would enable native chemical ligation at any site in a peptide backbone, not just at cysteine residues.

The Staudinger reaction, which involves reaction between trivalent phosphorous compounds and organic azides (Staudinger et al. *Helv. Chim. Acta* 1919, 2, 635), has been used for a multitude of applications. (Gololobov et al. *Tetrahedron* 1980, 37, 437); (Gololobov et al. *Tetrahedron* 1992, 48, 1353). There are almost no restrictions on the nature of the two reactants. The phosphines can be cyclic or acyclic, halogenated, bisphosphorus, or even polymeric. Similarly, the azides can be alkyl, aryl, acyl or phosphoryl. The one restriction on all of the reactions mentioned thus far is that they were carried out, or at least initiated, under oxygen-free anhydrous conditions since most phosphorus (III) compounds are readily oxidized and many are susceptible to hydrolysis.

The mechanism of the reaction has been studied in detail (Leffler et al. *J. Am. Chem. Soc.* 1967, 89, 5235). As illustrated below, the first intermediate is the adduct formed by the attack of the phosphorus lone pair on the terminal nitrogen of the azide. The phosphazide decomposes with the loss of $N_2$ to form an aza-ylide via a 4-membered ring transition state. The aza-ylide can be isolated if the substituents are able to stabilize the highly nucleophilic nitrogen atom and electrophilic phosphorus atom. However, when water is added to the reaction mixture the aza-ylide rapidly hydrolyzes to form a phosphine oxide and an amine. Depending on the concentration of the reactants in solution and the electronic and steric nature of the substituents, the rate determining step can be either the association to form the phosphazide, or its breakdown to the aza-ylide (Gololobov et al. *Tetrahedron* 1992, 48, 1353)

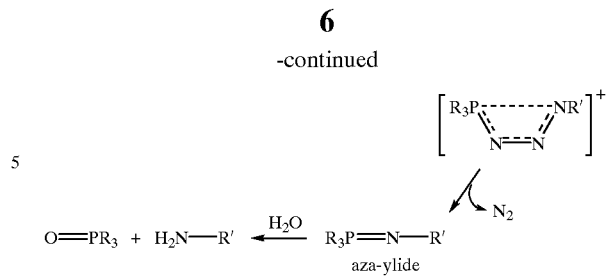

Traditionally the Staudinger reaction has simply entailed the reduction of azide functionalities to amines by triphenylphosphine initiated under anhydrous conditions. However, several reported reactions take advantage of the reactivity of the aza-ylide to carry out chemical transformations besides hydrolysis to the amine, some even in the presence of water. When the phosphorus compound possesses at least one alkoxy substituent, the aza-ylide undergoes an Arbuzov-like rearrangement resulting in a new covalent linkage, as shown in reaction (a) below (Keogh et al. *J. Org. Chem.* 1986, 51, 2767). Triphenylphosphine can be used to mediate the formation of amide bonds without the need for an activated ester (see reaction (b) below). (Wilt et al. *J. Org. Chem.* 1985, 50, 2601). In addition, an aza-ylide can be trapped by an intramolecular electrophile such as an alkyl halide ((c) below), (Mastryukova et al. *Zh. Obshch. Khim.* 1988, 58, 1967) or ester ((d) below), (Khoukhi et al. *Tetrahedron Lett.* 1986, 27, 1031).

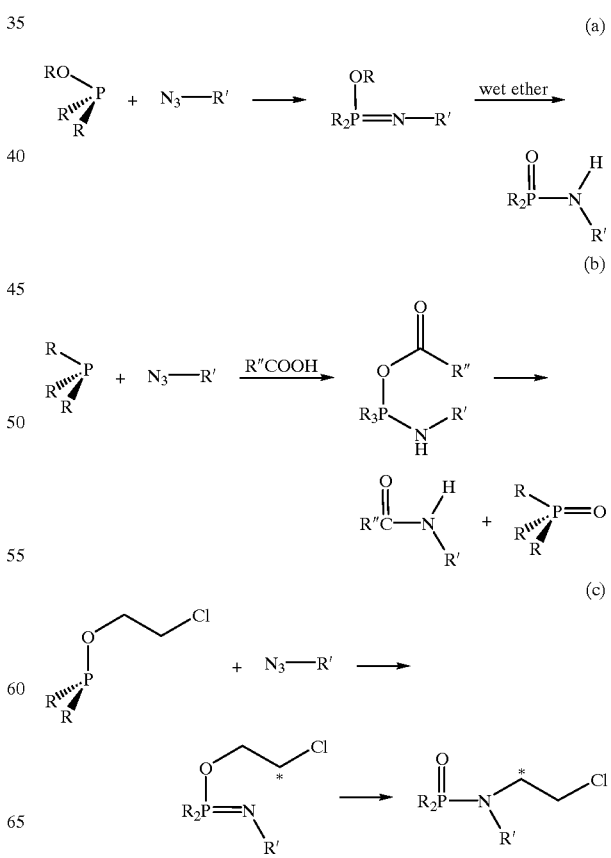

-continued

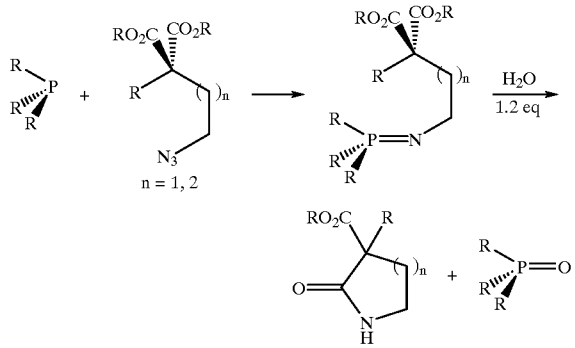

(d)

Prior to the present disclosure, the Staudinger reaction has never been adapted to perform ligations in a biological environment. Both reactants are intrinsically orthogonal to biological molecules and yet the azide is readily installed in carbohydrates or proteins. The reaction between the phosphine and the azide must produce a stable covalent adduct and utilize a phosphorus compound that is stable to water and air. Reactions (a) and (d) above appear to fulfill this latter requirement as they are carried out in the presence of a small amount of water, however it was unknown whether this reactivity would extend to truly aqueous conditions.

There is a need in the field for additional mechanisms to modify biological molecules through chemoselective ligations, particularly in a biological environment. The present invention addresses this need.

SUMMARY OF THE INVENTION

The present invention features a chemoselective ligation reaction that can be carried out under physiological conditions. In general, the invention involves condensation of a specifically engineered phosphine, which can provide for formation of an amide bond between the two reactive partners resulting in a final product comprising a phosphine oxide, or which can be engineered to comprise a cleavable linker so that a substituent of the phosphine is transferred to the azide, releasing an oxidized phosphine byproduct and producing a native amide bond in the final product. The selectivity of the reaction and its compatibility with aqueous environments provides for its application in vivo (e.g., on the cell surface or intracellularly) and in vitro (e.g., synthesis of peptides and other polymers, production of modified (e.g., labeled) amino acids).

DETAILED DESCRIPTION OF THE INVENTION

Figure 1:
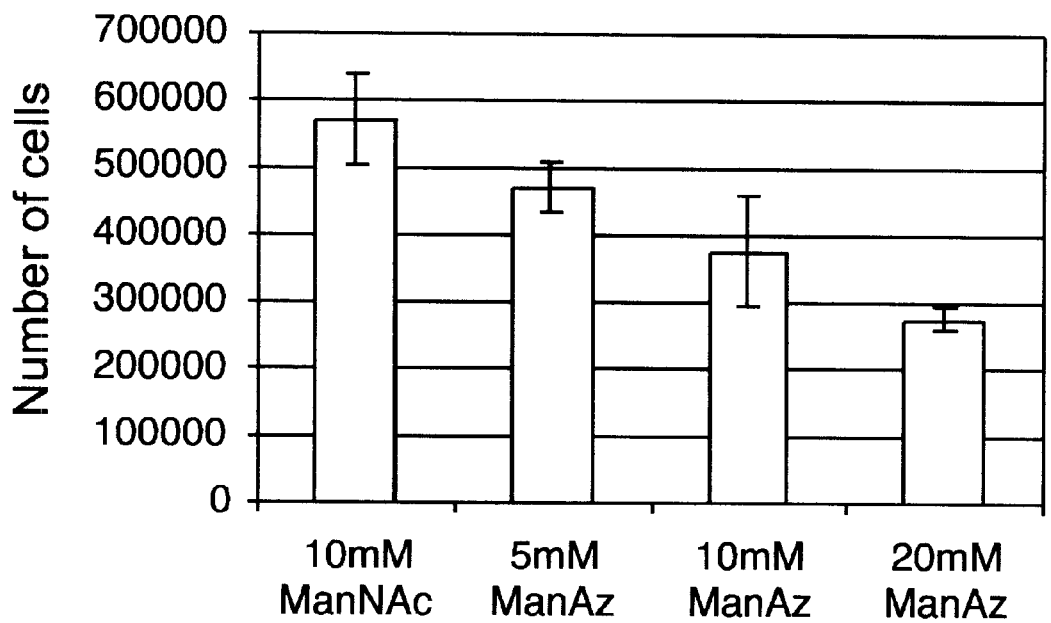
FIG. 1 is a graph showing the effect of ManAz on the growth of Jurkat cells. Error bars represent the standard deviation of the mean for three experiments.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a biomolecule" includes a plurality of such biomolecules, and reference to "the cell"

includes reference to one or more cells and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

By "reactive partner" is meant a molecule or molecular moiety that specifically reacts with another reactive partner. Exemplary reactive partners are those of the reaction of the invention, i.e., an azide and an engineered phosphine moiety.

By "engineered phosphine moiety" (also referred to herein as "engineered phosphine") is meant a moiety comprising a phosphine and an electrophilic moiety, which engineered phosphine moiety, when reacted with an azide, provides for production of a covalent linkage between the engineered phosphine moiety and the azide or, where the engineered phosphine moiety further comprises a cleavable linker, an native amide bond between the molecules comprising the reactive partners and the production of oxidized phosphine.

By "cleavable linker" is meant a moiety suitable for use in an engineered phosphine moiety that, following reaction of the engineered phosphine moiety with an azide, facilitates intramolecular rearrangement to provide for a native amide bond and production of oxidized phosphine.

As used herein the term "isolated" is meant to describe a compound of interest that is in an environment different from that in which the compound naturally occurs. "Isolated" is meant to include compounds that are within samples that are substantially enriched for the compound of interest and/or in which the compound of interest is partially or substantially purified.

As used herein, the term "substantially purified" refers to a compound that is removed from its natural environment and is at least 60% free, preferably 75% free, and most preferably 90% free from other components with which it is naturally associated.

As used herein, the term "cell" in the context of the in vivo applications of the invention is meant to encompass eukaryotic and prokaryotic cells of any genus or species, with mammalian cells being of particular interest. "Cell" is also meant to encompass both normal cells and diseased cells, e.g., cancerous cells.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

The term "physiological conditions" is meant to encompass those conditions compatible with living cells, e.g., predominantly aqueous conditions of a temperature, pH, salinity, etc. that are compatible with living cells.

The term "aryl" as used herein means 5- and 6-membered single-aromatic radicals which may include from zero to four heteroatoms. Representative aryls include phenyl, thienyl, furanyl, pyridinyl, (is)oxazoyl and the like.

The term "lower alkyl", alone or in combination, generally means an acyclic alkyl radical containing from 1 to about 10, preferably from 1 to about 8 carbon atoms and more preferably 1 to about 6 carbon atoms. Examples of such radicals include methyl, ethyl, n-propyl, isopropyl, n-butyl, isobutyl, sec-butyl, tert-butyl, pentyl, iso-amyl, hexyl, octyl and the like.

Overview

The invention provides, for the first time, methods and compositions for specifically and efficiently synthetically modifying cellular components in an aqueous environment, thus providing for modification of such cellular components on or in living cells. The invention uses reactive partners that are completely abiotic and are chemically orthogonal to native cellular components, thus providing for extreme selectivity of the reaction. Furthermore, the reaction can be carried out under physiological conditions, e.g., a pH of about 7 within an aqueous environment, and at about 37° C.

The invention is based on the discovery of a means for carrying out a modified Staudinger reaction that can be carried out in an aqueous environment. Because the reaction of the invention is highly selective and functions in both aqueous and organic solvents, the reaction can be used in a variety of applications both in vitro and in vivo. The reaction is accomplished through use of a first molecule comprising a phosphine reactant engineered to comprise an electrophilic moiety that serves as an aza-ylide trap, and second molecule comprising an azide moiety. The specifically engineered phosphine can be engineered to provide for formation of an amide bond between these two reactive partners resulting in a final conjugate product comprising a phosphine moiety. The first molecule comprising the phosphine moiety can further comprise a moiety that allows for subsequent reactions and/or which provides for detectable labeling of the product of the final reaction. Alternatively, the phosphine can be engineered to comprise a cleavable linker so that a substituent of the phosphine is transferred to the azide, releasing an oxidized phosphine as a byproduct and producing a native amide bond in the final product.

Various aspects of the invention will now be described in more detail.

Chemoselective Ligation to Provide an Covalent Bond Between Reactants with a Final Product Comprising a Phosphine Moiety In one embodiment, the chemoselective ligation is designed for use in fully aqueous, physiological conditions and involves production of a stable, final product comprising a phosphine moiety. In general, this embodiment involves reacting a first reactant comprising an engineered phosphine comprising an electrophilic trap with a second reactant comprising an azide such that a covalent bond is formed between the first and second reactants by intramolecular rearrangement of an aza-ylide intermediate. The ideal reactants are readily synthetically accessible, fully water soluble, stable under biological conditions, and react rapidly and efficiently at low concentrations to produce a covalently bound product. Until the present disclosure, no chemoselective reaction based on the use of a phosphine moiety and encompassing all of these characteristics has been reported.

The engineered phosphine is generally of the formula

Y-Z-PR$_2$R$_3$ where

Z is an aryl group substituted with R$_1$, wherein R$_1$ is preferably in the ortho position on the aryl ring relative to the PR$_2$R$_3$; and wherein R$_1$ is an electrophilic group to trap (e.g., stabilize) an aza-ylide group, including, but not necessarily limited to, a carboxylic acid, an ester (e.g., alkyl ester (e.g., lower alkyl ester, benzyl ester), aryl ester, substituted aryl ester), aldehyde, amide, e.g., alkyl amide (e.g., lower alkyl amide), aryl amide, alkyl halide (e.g., lower alkyl halide), thioester, sulfonyl ester, alkyl ketone (e.g., lower alkyl ketone), aryl ketone, substituted aryl ketone, halosulfonyl, nitrile, nitro and the like;

R$_2$ and R$_3$ are generally aryl groups, including substituted aryl groups, or cycloalkyl groups (e.g., cyclohexyl groups) where R$_2$ and R$_3$ may be the same or different, preferably the same; and Y is H, a reactive group that facilitates covalent attachment of a molecule of interest, or a molecule of interest, wherein Y can be at any position on the aryl group (e.g., para, meta, ortho); where exemplary reactive groups include, but are not necessarily limited to, carboxyl, amine, (e.g., alkyl amine (e.g., lower alkyl amine), aryl amine), ester (e.g., alkyl ester (e.g., lower alkyl ester, benzyl ester), aryl ester, substituted aryl ester), thioester, sulfonyl halide, alcohol, thiol, succinimidyl ester, isothiocyanate, iodoacetamide, maleimide, hydrazine, and the like. Exemplary molecules of interest further include dyes (e.g., fluorescein or modified fluorescein, and the like), toxins (including cytotoxins), linkers, peptides, and the like.

The molecule of interest may be reacted directly with the reactive group or through a linker. Exemplary molecules of interest include, but are not necessarily limited to, a detectable label, a small molecule, a peptide, and the like. Such molecules of interest are described in more detail below.

In one embodiment of particular interest, the engineered phosphine reactant is generally of the formula:

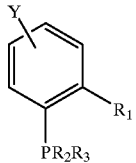

Thus, in general, the engineered phosphine reactant can serve as a bifunctional molecule that facilitates covalent crosslinkage of two molecules of interest. Preferably the phosphine reactant is a triaryl phosphine, where R$_1$ is an alkyl or sulfonyl ester. An exemplary and preferred engineered phosphine reactant is 2-diphenylphosphanyl-benzoic acid methyl ester.

The second reactant comprises an azide. Molecules comprising an azide and suitable for use in the present invention, as well as methods for producing azide-comprising molecules suitable for use in the present invention, are well known in the art. Target molecules of particular interest as the second reactant include, but are not necessarily limited to, amino acids and amino acid residues, polypeptides (including peptides and proteins), sugars or sugar residues, and the like which contain or are modified to contain at least one azide. The polypeptides may be composed of D-amino acids, L-amino acids, or both, and may be further modified, either naturally, synthetically, or recombinantly, to include other moieties. For example, the target polypeptide may be a lipoprotein, a glycoprotein, or other such modified protein. The target molecules can be naturally occurring, or may be synthetically or recombinantly produced, and may be isolated, substantially purified, or present within the native milieu of the unmodified molecule upon which the azide-containing target molecule is based (e.g., on a cell surface or within a cell, including within a host animal, e.g., a mammalian animal, such as a murine host (e.g., rat, mouse), hamster, canine, feline, bovine, swine, and the like).

In general, the target molecule useful as the second reactant comprises at least one azide for reaction with an engineered phosphine according to the invention, but may comprise 2 or more, 3 or more, 5 or more, 10 or more azides. The number of azides that may be present in a target molecule will vary according to the intended application of the final product of the reaction, the nature of the target molecule itself, and other considerations which will be readily apparent to the ordinarily skilled artisan in practicing the invention as disclosed herein.

This embodiment of the invention is particularly useful in modification of a target molecule in vivo. In this embodiment, the target substrate is modified to comprise an azide group at the point at which linkage to the engineered phosphine reactant is desired. For example, where the target substrate is a polypeptide, the polypeptide is modified to contain an N-terminal azide. Where the target substrate is a glycoprotein, a sugar residue of the glycoprotein can be modified to contain an azide.

The target substrate can be generated in vitro and then introduced into the cell using any of a variety of methods well known in the art (e.g., microinjection, liposome or lipofectin-mediated delivery, electroporation, etc.), which methods will vary according to the nature of the substrate to be targeted for modification and can be readily and appropriately selected by the ordinarily skilled artisan. The final target substrate can also be generated in vivo by exploiting a host cell's natural biosynthetic machinery. For example, the cell can be provided with a biocompatible azide-derivative of a substrate for synthesis of the desired target molecule, which substrate is processed by the cell to provide an azide-derivative of the desired final target substrate. For example, where the target substrate is a cell surface glycoprotein, the cell can be provided with an azide derivative of a sugar residue found within the glycoprotein, which is subsequently processed by the cell through natural biosynthetic processes to produce a modified glycoprotein having at least one modified sugar moiety comprising an accessible azide group.

The target substrate can also be produced in vivo using methods well known in the art. For example, unnatural amino acids having azides can be incorporated into recombinant polypeptides expressed in *E. coli* (see, e.g., Kiick et al. Tetrahedron (2000) 56:9487). Such recombinantly produced polypeptides can be selectively reacted with a phosphine reagent according to the invention.

Expression of an Abiotic Reactant on the Cell Surface

The expression of an abiotic reactive partner (e.g., an azide or a phosphine moiety) to cell surfaces can significantly expand applications of cell surface engineering. Since azides and phosphines are abiotic structures both inside and outside cells, and since the reaction of the invention can be carried out under physiological conditions, the reaction can be used in both extracellular and intracellular environments.

In one example, the abiotic reactive partner is incorporated into the target substrate by providing the cell with a synthetic building block for the desired biopolymer target substrate. For example, the cell can be provided with a sugar molecule comprising an abiotic reactive partner to provide for incorporation of the abiotic reactive partner in a glycoprotein which is in turn expressed on the cell surface. Alternatively, the abiotic reactive partner can be incorporated into an amino acid, which is subsequently incorporated into a peptide or polypeptide synthesized by the cell. Several methods are available for incorporating unnatural building blocks into biopolymers, one need not be restricted to cell surface oligosaccharides as hosts for these chemical handles (vanHest et al. *FEBS Lett.* 1998, 428, 68; Nowak et al. *Science* 1995, 268, 439). The introduction of the reactive partners into transiently associated biopolymers might allow their covalent trapping within a cell and, as a result, the identification of previously unobservable interactions.

Therefore, in one aspect, the invention features a method of expressing an abiotic reactive partner (e.g., an azide or an engineered phosphine) on the surface of a host cell. The surface abiotic reactive partner can then be reacted with its counterpart to provide for chemoselective ligation at the cell surface.

In one embodiment, the synthetic substrate comprising an abiotic reactive partner for incorporation into a biopolymer is an azide derivative of a sugar utilized in production of a cell surface molecule, e.g., in the glycoprotein biosynthetic pathway. For example, the host cell can be provided with a synthetic sialic acid azido-derivative, which is incorporated into the pathway for sialic acid biosynthesis, eventually resulting in the incorporation of the synthetic sugar residue in glycoproteins, which are in turn presented on the cell surface.

In one example, the synthetic substrate is an azido derivative of mannosamine of the general formula:

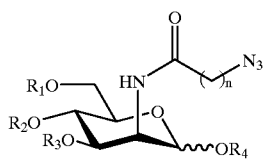

where n is from 1 to 6, generally from 1 to 4, more usually 1 to 2, and $R_1$, $R_2$, $R_3$, and $R_4$ are independently hydrogen or acetyl. Preferably, the substrate is N-azidoacetylmannosamine (n=1) or an acetylated derivative thereof, or N-azidopropanoylmannosamine (n=2) or an acetylated form thereof.

In another embodiment, the synthetic substrate is an azido sugar derivative of a general formula of, for example:

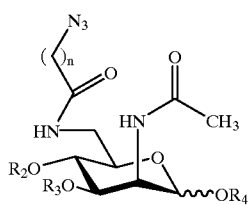

-continued

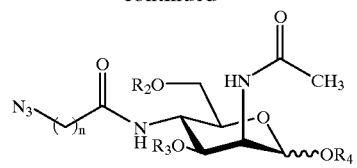

either of which can be incorporated into the sialic acid biosynthesis pathway, and where n is from 1 to 6, generally from 1 to 4, more usually 1 to 2, and $R_2$, $R_3$, and $R_4$ are independently hydrogen or acetyl.

In another embodiment, the synthetic substrate is an azido sugar derivative of a general formula of, for example:

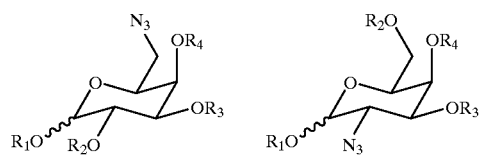

where $R_1$, $R_2$, $R_3$, and $R_4$ are independently hydrogen or acetyl, and where the synthetic substrate is incorporated into biosynthetic pathways involving fucose.

In another embodiment, the synthetic substrate is an azido sugar derivative of a general formula of, for example:

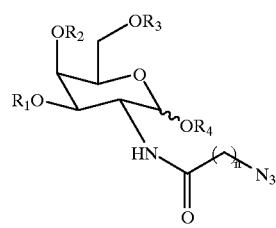

where n is from 1 to 6, generally from 1 to 4, more usually 1 to 2, and $R_1$, $R_2$, $R_3$, and $R_4$ are independently hydrogen or acetyl, and which is incorporated into biosynthetic pathways involving galactose.

Delivery of Detectable Labels, Drugs, and Other Molecules to an Target Substrate Comprising an Abiotic Reactive Moiety The engineered phosphine can be modified to comprise a molecule desired for delivery and conjugation to the azido-target substrate, which target substrate may be expressed on the cell surface (e.g., as described above), may reside within the cell membrane, or may be intracellular. Molecules that may be desirable for delivery include, but are not necessarily limited to, detectable labels (e.g., spin labels, FRET-type dyes, e.g., for studying structure of biomolecules in vivo), small molecule drugs, cytotoxic molecules (e.g., drugs), ligands for binding by a target receptor (e.g., to facilitate viral attachment, attachment of a targeting protein present on a liposome, etc.), tags to aid in purification by, for example, affinity chromatography (e.g., attachment of a FLAG epitope), and molecules to facilitate selective attachment of the polypeptide to a surface, and the like. Specific, non-limiting examples are provided below.

Detectable Labels.

The compositions and methods of the invention can be used to deliver a detectable label to a target molecule having an azide. Exemplary detectable labels include, but are not necessarily limited to, fluorescent molecules (e.g., autofluorescent molecules, molecules that fluoresce upon contact with a reagent, etc.), radioactive labels (e.g., $^{111}$In, $^{125}$I, $^{131}$I, [212]B, $^{90}$Y, [186]Rh, and the like); biotin (e.g., to be detected through reaction of biotin and avidin); fluorescent tags; imaging reagents (e.g., those described in U.S. Pat. Nos. 4,741,900 and 5,326,856), and the like. Detectable labels also include peptides or polypeptides that can be detected by antibody binding, e.g., by binding of a detectably labeled antibody or by detection of bound antibody through a sandwich-type assay.

In one embodiment, the invention provides an engineered phosphine that acts as an azide-selective phosphine dye. In this embodiment, the dye remains substantially undetectable until reaction with an azide. In general, the phosphorous lone pair renders the dye substantially undetectable (e.g., substantially non-fluorescent) until reaction with an azide, when the lone pair is removed from conjugation by formation of a phosphine oxide. The unmasked dye provides for a detectable signal following reaction with the azide of the target molecule according to the invention. This reaction can be generally represented as follows:

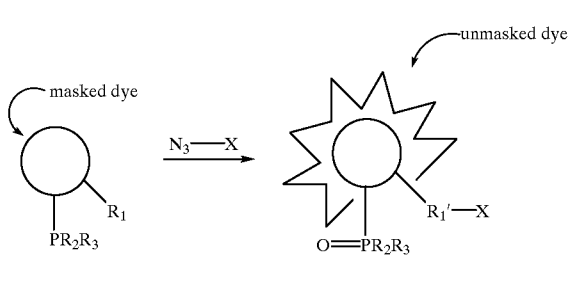

where the masked dye generally comprises an aryl group substituted with $R_1$ and $PR_2R_3$;

$R_1$ is an electrophilic group to trap (e.g., stabilize) an aza-ylide group, including, but not necessarily limited to, a carboxylic acid, an ester (e.g., alkyl ester (e.g., lower alkyl ester, benzyl ester), aryl ester, substituted aryl ester), aldehyde, amide, e.g., alkyl amide (e.g., lower alkyl amide), aryl amide, alkyl halide (e.g., lower alkyl halide), thioester, sulfonyl ester, alkyl ketone (e.g., lower alkyl ketone), aryl ketone, substituted aryl ketone, halosulfonyl, nitrile, nitro and the like;

$R_2$ and $R_3$ are generally aryl groups, including substituted aryl groups, or cycloalkyl groups (e.g., cyclohexyl groups) where $R_2$ and $R_3$ may be the same or different, preferably the same;

$R_1$ and $PR_2R_3$ are preferably in the ortho position relative to one another on an aryl ring of the dye, or in an equivalent position that provides for the reaction to proceed according to the invention;

X represents a target molecule having an azide $N_3$; and where $R_1'$ represents a modified $R_1$ group following reaction with the azide of the target molecule via the Staudinger ligation reaction described herein.

A specific example of this reaction can be generally represented as follows:

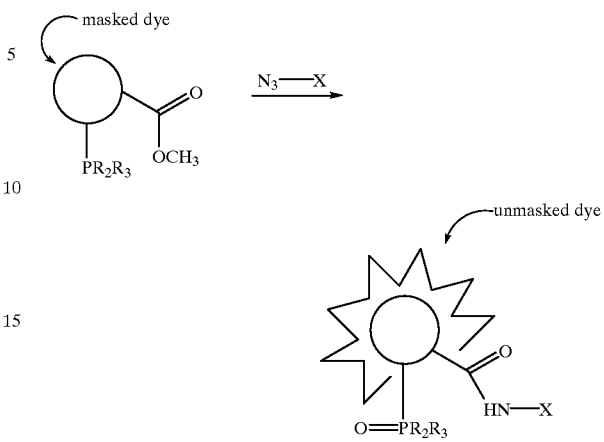

In one exemplary embodiment, the phosphine dye is a fluorescein derivative, which may be in unacetylated or acetylated (cell permeable) form. In one embodiment the phosphine dye is of the formula:

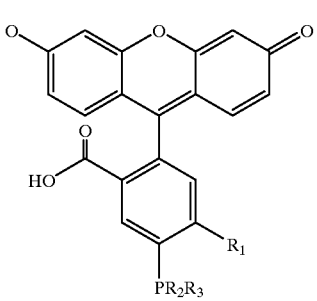

where $R_1$ is an electrophilic group to trap (e.g., stabilize) an aza-ylide group as described above, and $R_2$ and $R_3$ are generally aryl groups, including substituted aryl groups, or cycloalkyl groups (e.g., cyclohexyl groups) where $R_2$ and $R_3$ may be the same or different, preferably the same.

In a specific exemplary embodiment, the phosphine dye is of one of the formulas:

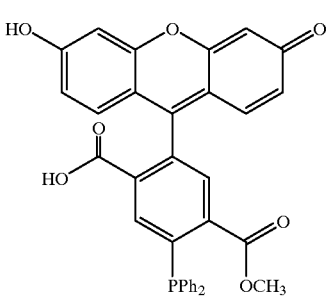

-continued

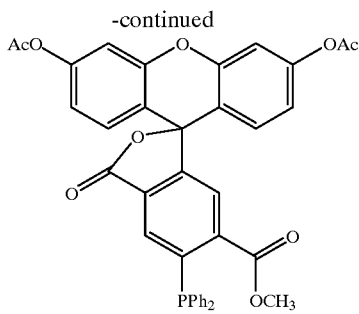

where Ph represents phenyl groups, including substituted phenyl groups.

The phosphine dye of the invention can be used to detect an azide on any molecule, with biomolecules being of particular interest. Furthermore, the phosphine dye can be used to detected biomolecules having an azide at the cell surface or within cells, thus providing the basis for extracellular and intracellular probes.

Attachment of Target Molecules to a Support

The engineered phosphine can also comprise one or more hydrocarbon linkers (e.g., an alkyl group or derivative thereof) conjugated to a moiety providing for attachment to a solid substratum (e.g., to facilitate assays), or to a moiety providing for easy separation (e.g., a hapten recognized by an antibody bound to a magnetic bead). In one embodiment, the methods of the invention are used to provide for attachment of a protein (or other molecule that contains or can be modified to contain an azide) to a chip in a defined orientation. For example, a polypeptide having an azide at a selected site (e.g., at or near the N-terminus) can be generated, and the methods and compositions of the invention used to deliver a tag or other moiety to the azide of the polypeptide. The tag or other moiety can then be used as the attachment site for affixing the polypeptide to a support (e.g., solid or semi-solid support, particular a support suitable for use as a microchip in high-throughput assays).

Attachment of Molecules for Delivery to a Target Site

The engineered phosphine can comprise a small molecule drug, toxin, or other molecule for delivery to the cell and which can provide for a pharmacological activity or can serve as a target for delivery of other molecules.

In another embodiment, the engineered phosphine comprises one of a pair of binding partners (e.g., a ligand, a ligand-binding portion of a receptor, etc.). For example, the engineered phosphine can comprise a polypeptide that serves as a viral receptor and, upon binding with a viral envelope protein or viral capsid protein, facilitates attachment of virus to the cell surface on which the engineered phosphine is expressed. Alternatively, the engineered phosphine comprises an antigen that is specifically bound by an antibody (e.g., monoclonal antibody), to facilitate detection and/or separation of host cells expressing cell surface phosphine. In another example, the engineered phosphine comprises a ligand binding portion of a receptor, or a receptor-binding portion of a ligand.

Synthesis of Modified Polypeptides Comprising Oxidized Phosphine

In another embodiment, the methods described herein can be used to generate a polypeptide having any desired number of amino acids modified according to the invention. The modified polypeptide so produced is at least 2 amino acid residues in length (with at least one amino acid residue being modified according to the invention), and may comprise up to 100 amino acids to 500 amino acids or more (e.g., 3 to 5 amino acid residues, 10 to 50 amino acid residues, 25 to 150 amino acid residue), up the a full-length native protein or more (e.g., a native protein having additional amino acid residues). The ratio of amino acids modified versus not modified according to the invention can be selected as desired to the intended use of the modified polypeptide.

As will be readily appreciated by the ordinarily skilled artisan upon reading the present specification, the production of an amide bind between a compound comprising an azide and a compound comprising a phosphine engineered according to the invention has a wide variety of applications both in vitro and in vivo, which variations are within the scope of the invention.

Chemoselective Ligation to Produce Amide Bond Between Reactants

In one embodiment of the invention, the chemoselective ligation is performed with a first reactant comprising a phosphine group as described above, except modified to comprise a cleavable linker. In this embodiment, the engineered phosphine reactant comprises a cleavable linker and is of the general formula:

$$X_1\text{-}Y\text{-}R_4\text{-}PR_2R_3$$

where $X_1$ is a first molecule of interest (e.g., a detectable label, a small molecule, a peptide, a reactive moiety for further extension of the molecule upon completion of the first reaction, and the like and combinations thereof), which molecule may be bonded either directly or through a linker group, and which molecule is desired to be attached to a second molecule of interest via an amide bond;

Y is an electrophile, preferably carbonyl or thiocarbonyl which acts as a cleavable linker;

$R_4$ is a linker to the electrophile, and may be an alkyl or a substituted or unsubstituted aryl group; and $R_2$ and $R_3$ are generally aryl groups, including substituted aryl groups, or cycloalkyl groups (e.g., cyclohexyl groups), where $R_2$ and $R_3$ may be the same or different, preferably the same.

Suitable R4-PR2R3 moieties include, but are not necessarily limited to:

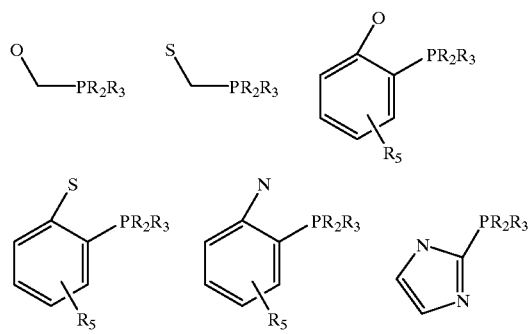

where $R_1$ is preferably in the ortho position on the aryl ring relative to the $PR_2R_3$; and $R_5$ is a substituent comprising an electron-withdrawing or electron-donating group that electronically or sterically modifies the reactivity of the N, O, or S atom (e.g. a halide group (e.g. Cl), a methyl group, or a methoxy group, and the like).

In specific exemplary embodiments, $R_4$-$PR_2R_3$ is one of:

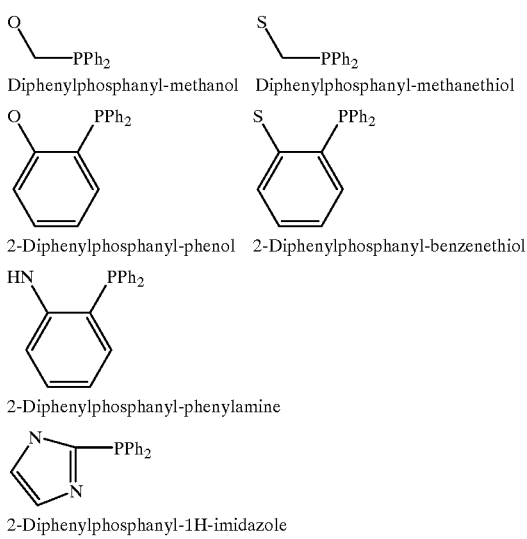

In one embodiment of particular interest, $R_4$-$PR_2R_3$ is a methylphosphine ester.

In general, reaction of a i) first reactant comprising a first molecule of interest and an engineered phosphine comprising a cleavable linker with ii) a second reactant comprising a second molecule of interest and an azide results in conjugation of the first molecule of interest to the second molecule of interest via an amide or a thioamide bond, accompanied by the release of nitrogen and an oxidized phosphine byproduct. An example of this reaction is illustrated below:

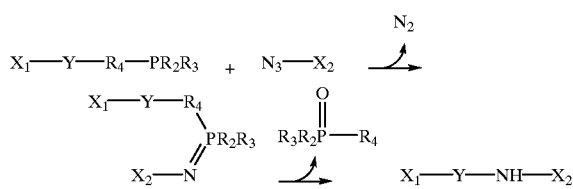

In this reaction, $X_1$ and $X_2$ can be the same or different compounds for which production of an amide-linked polymer is desired. In one embodiment of interest, $X_1$ and $X_2$ are peptides, which peptides may be of the same or different amino acid composition and/or sequence. As used herein "peptide" is meant to encompass a polymer of at least two or more amino acids, which amino acids may be naturally-occurring, unnatural, or modified. $X_1$ and/or $X_2$ are peptides, the peptide an amino acid or a peptide comprising at least 2 amino acid residues up to 100 amino acids to 500 amino acids or more, e.g., 3 to 5 amino acid residues, 10 to 50 amino acid residues, 25 to 150 amino acid residue, etc.

This embodiment of the invention can be used in a variety of applications, e.g., to selectively attach a small molecule to an engineered or semi-synthetic polymer. The invention can be performed in solution, or can be performed on solid phase, allowing functionalization of surfaces and the facile construction of libraries of small molecules. As will be readily appreciated by the ordinarily skilled artisan upon reading the present specification, such various applications that take advantage of the production of a native amide linkage between a compound comprising an azide and a compound comprising a phosphine engineered according to the invention has a wide variety of applications, which variations are within the scope of the invention.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Methods and Materials

The following procedures are used in the Examples described in detail below. Although some of the methods described below are in common use, the specific protocol used in the Examples below is described in detail where alternative protocols are often employed. Basic procedures are not described, as such are well within the skill of the ordinarily skilled artisan and, in some instances, are carried out with a kit and/or according to the reagent manufacturer's instructions.

All chemical reagents were of analytical grade, obtained from commercial suppliers and used without further purification unless otherwise noted. All reaction solvents were distilled under a nitrogen atmosphere. THF was dried and deoxygenated over benzophenone and Na°, $CH_2Cl_2$, pyridine and $CH_3CN$ were dried over $CaH_2$, MeOH was dried over Mg° and toluene was dried over Na°. Water used in biological procedures was doubly distilled and deionized using a Milli-Q™ system (Millipore). All solvents were concentrated under reduced pressure using a rotary evaporator.

Chromatography

Thin layer chromatography was performed using Analtech Uniplate silica gel plates. Compounds were visualized by staining with ceric ammonium molybdate, triphenylphosphine followed by ninhydrin (for azides) and/or by the absorbance of UV light. Flash chromatography was performed using Merck 60 Å 230-400 mesh silica gel. Chromatography solvents were used without distillation.

Spectra

All $^1H$ and $^{13}C$ NMR spectra were measured with a Bruker AMX-300, AMX-400 or DRX-500 MHz spectrometer as noted. Chemical shifts are reported in $\delta$ relative to tetramethylsilane for $^1H$ and $^{13}C$ spectra and relative to $H_3PO_4$ for $^{31}P$ spectra. Coupling constants (J) are reported in Hz. Fast Atom Bombardment (FAB), Chemical Ionization (CI) and Electrospray (ES) mass spectra were obtained at the UC Irvine and UC Berkeley Mass Spectrometry Laboratories. Elemental analyses were obtained at the UC Berkeley Microanalytical Laboratory. Infrared spectra were taken on a Perkin Elmer series Fourier transform infrared spectrometer. Uncorrected melting points were determined in glass capillaries using a Thomas Hoover oil bath apparatus.

Jurkat Cell Cultures

Cell cultures of Jurkat were maintained in RPMI 1640 media (Gibco Laboratories, Grand Island, N.Y.) supplemented with 5% fetal bovine serum (FBS, Hyclone, Logan, Utah), 50 units/mL of penicillin and 50 μg/mL of streptomycin (Mediatech, Herndon, Va.), in a humidified 5% $CO_2$ atmosphere at 37° C. Cell densities were determined using a Coulter Counter-Z2 (Coulter, Miami, Fla.).

Flow Cytometry

Flow cytometry analysis was performed on a Coulter EPICS® XL-MCL cytometer (Coulter, Miami, Fla.) using a 488 nm argon laser. At least $10^4$ viable cells were analyzed from each sample. Dead cells were excluded from the analysis using forward/side scatter gating.

Synthesis of 1-azido-11-hydroxy-3,6,9-trioxaundecane (Compound 6)

To a solution of dry triethylamine (TEA) (50.0 mL, 0.360 mol) and tetraethylene glycol (44.4 mL, 0.260 mol) in $CH_2Cl_2$ (200 mL) was added MsCl (10.0 mL, 0.130 mol) via syringe over a period of 3 h. The white suspension was allowed to warm to room temperature (rt) and the solvent was removed in vacuo. The crude reaction mixture was dissolved in 300 mL of EtOH and $NaN_3$ (27.0 g, 0.420 mmol) was added. The suspension was heated at reflux for 24 h. After cooling to rt, the reaction mixture was concentrated and co-evaporated with toluene (4×20 mL). The residue was diluted with $Et_2O$ (400 mL), washed with sat. NaCl (2×100 mL) and dried over $Na_2SO_4$. The crude product was purified by silica gel chromatography eluting with a gradient of 1:1 to 4:1 EtOAc/hexanes to afford 20 g (70%) of a viscous oil. $^1H$ NMR (400 MHz, $CDCl_3$): δ3.12 (s, 1H), 3.26 (t, 2H, J=4.8), 3.45–3.47 (m, 2H), 3.53–3.55 (m, 10H), 3.56–3.59 (m 2H). (Bertozzi et al. *J. Org. Chem.* 1991, 56, 4326)) $^1H$ NMR (500 MHz, $CDCl_3$): δ2.54 (br t, 1H, J=5.9), 3.37 (t, 2H, J=5.2), 3.58–3.60 (m, 2H), 3.64–3.67 (m, 10H), 3.69–3.72 (m, 2H). HRMS (CI): m/z 220.1293 (MH+$C_8H_{18}N_3O_4$ requires 220.1297).

Synthesis of Compound 8

To a solution of compound 6 (42 mg, 0.19 mmol) in THF (1.1 mL) and $H_2O$ (1.1 mL) was added methyl diphenylphosphinite (46 μL, 0.23 mmol). The resulting solution was stirred under $N_2$ for 2 h and then concentrated. The excess starting material was removed via filtration through a plug of silica gel eluting with EtOAc. The filtrate was concentrated to provide 67 mg (91%) of a colorless oil. IR (thin film): 3375, 2874, 1646, 1436, 1181, 1123, 942 $cm^{-1}$. $^1H$ NMR (300 MHz, $CDCl_3$): δ2.97 (s, 1H), 3.06–3.15 (m, 4H), 3.56–3.62 (m, 12H), 7.41–7.46 (m, 5H), 7.85–7.91 (m, 5H). $^{13}C$ NMR (125 MHz, $CDCl_3$): δ40.5, 61.2, 69.9, 70.0, 70.4, 70.5, 72.5, 72.6, 128.3, 128.4, 131.6, 132.1, 132.2. $^{31}P$ NMR (160 MHz, $CDCl_3$): δ25.109. HRMS (CI): m/z 394.1789 (MH+$C_{20}H_{29}NO_5P$ requires 394.1783).

Synthesis of Compound 13 (2-diphenylphosphanyl-methylbenzoate) (Stelzer et al *J. Organomet. Chem.* 1996, 522, 69)

To a flame-dried flask was added $CH_3CN$ (21 mL), TEA (1.4 mL, 9.4 mmol), 2-iodomethylbenzoate (1.4 mL, 9.4 mmol) and palladium acetate (2.2 mg, 0.01 mmol). The mixture was degassed in vacuo before diphenylphosphine (1.6 mL, 9.4 mmol) was added to the flask via syringe under an atmosphere of Ar. The resulting solution was heated at reflux for 4 h, at which point it was cooled to rt and concentrated. The residue was dissolved in 250 mL of 1:1 $Et_2O/H_2O$ and the layers were separated. The organic layer was concentrated, dried over $Na_2SO_4$ and the product was purified via silica gel chromatography eluting with 50:1 EtOAc/hexanes. The pure product was obtained as 2.0 g (66%) of a white crystalline solid, mp 95–96° C. (lit. 96° C.). (Rauchfuss et al. *J. Am. Chem. Soc.* 1981, 103, 6769) IR (thin film): 3052, 3000, 2648, 2839, 1719, 1584 $cm^{-1}$. $^1H$ NMR (400 MHz, $CDCl_3$): δ3.73 (s, 3H), 6.90–6.94 (m, 1H), 7.26–7.84 (m, 12H), 8.03–8.05 (m, 1H). $^{13}C$ NMR (125 MHz, $CDCl_3$): δ51.9, 128.2, 128.4, 128.5, 128.6, 130.7, 131.9, 133.8, 133.9, 134.2, 134.3, 137.8, 137.9, 140.3, 140.5, 167.2, 167.2. $^{31}P$ NMR (160 MHz, $CDCl_3$): δ−3.67. MS (CI) m/z 321 (MH+). Anal. Calcd for $C_{20}H_{17}O_2P$: C, 74.99; H, 5.35; Found: C, 74.75; H, 5.42.

General Method for Phosphine/Azide Coupling Reactions

The required amount of a stock solution of the azide was added to a round-bottom flask. The appropriate amount of solvent was added to bring the solution to the desired concentration, followed by the addition of the appropriate amount of a stock solution of the phosphine 13. The reaction mixture was stirred at rt and monitored by TLC at 30 min intervals until consumption of the limiting reagent was evident.

Preparation of N-2-(2-diphenylphosphinoyl)benzylamido-3, 4,6-triacetylgalactose (Mixture of Anomers) (18)

The general method was followed using 2-azido-2-deoxy-3,4,6-tri-O-acetyl galactoyl nitrate 16 (0.18 g, 0.50 mmol) and compound 13 (0.16 g, 0.50 mmol) in 10 mL of 3:1 $THF/H_2O$. The solution was stirred for 4 h and then concentrated. The pure product was isolated by silica gel chromatography eluting with a gradient of 1:4 EtOAc/hexanes to 100% EtOAc, to afford 0.12 g (37%) of a viscous oil. IR (thin film): 3252, 3058, 2961, 2243, 1742, 1659, 1532 $cm^{-1}$. $^1H$ NMR (400 MHz, $CDCl_3$): δ1.89 (s, 3H), 1.94 (s, 3H), 1.98 (s, 3H), 3.43 (s, 1H), 3.93 (br s, 1H), 4.36(br s, 2H), 4.98 (d, 1H, J=2.9), 5.24 (dd, 1H, J=8.2, 11.2), 5.34 (s, 1H), 6.83 (s, 1H), 6.99 (dd, 1H, J=7.7, 14.0), 7.20 (s, 1H), 7.55 (m, 12H). $^{13}C$ NMR (125 MHz, $CDCl_3$): δ20.7, 50.3, 62.0, 66.7, 67.6, 68.3, 77.4, 90.9, 128.3, 128.4, 128.8, 128.9, 129.6, 129.9, 131.5, 131.6, 131.7, 132.2, 132.3, 132.6, 132.7, 133.7, 133.8. $^{31}P$ NMR (160 MHz, $CDCl_3$): δ35.77. HRMS (ES) 632.1631 (MNa+$C_{31}H_{32}NNaO_{10}P$ requires 632.1661).

Preparation of 1-Methyl-N-2-(2-diphenylphosphinoyl) benzylamidogalactose (Mixture of Anomers) (19)

The general method was followed using 1-methyl-2-azido-2-deoxy-α-D-galactopyranoside 17 (51 mg, 0.23 mmol) and compound 13 (74 mg, 0.23 mmol) in 3 mL of 3:1 $THF/H_2O$. The solution was stirred for 5 h and then concentrated. The residue was dissolved in 10 mL of 1:1 $CH_2Cl_2/H_2O$ and the layers were separated. The aqueous layer was lyophilized to afford 85 mg (75%) of a white powder, mp 58–60 ° C. IR (thin film): 3362, 2937, 2113, 1650, 1548, 1438, 1266, 1119, 1070 $cm^{-1}$. $^1H$ NMR (300 MHz, $CDCl_3$): δ3.54 (s, 3H), 3.56–3.62 (m, 2H), 3.72–3.75 (m, 1H), 3.81–3.86 (m, 1H), 3.89–3.91 (m, 1H), 3.97–4.02 (m, 1H), 4.68 (d, 1H, J=8.4), 4.75 (d, 1H, J=3.8), 7.03–7.09 (m, 1H), 7.19–7.21 (m, 1H), 7.32–7.33 (m, 1H), 7.34–7.42 (m, 1H), 7.48–7.53 (m, 4H), 7.57–7.63 (m, 5H), 7.72–7.78 (m, 1H). $^{13}C$ NMR (125 MHz, $CDCl_3$): δ55.2, 55.3, 56.9, 57.1, 60.9, 61.7, 63.7, 63.8, 67.9, 68.3, 68.4, 72.2, 74.2, 103.2, 128.8, 128.9, 129.3, 131.9, 132.6, 170.0. $^{31}P$ NMR (160 MHz, $CDCl_3$): δ35.32. HRMS (ES) m/z: 520.1500 (MNa+$C_{26}H_{28}NNaO_7P$ requires 520.1501).

Synthesis of 2-Azidoacetic Acid (Compound 23)

To a solution of 2-bromoacetic acid (1.0 g, 7.2 mmol) in MeOH (7 mL) was added $NaN_3$ (0.940 g, 14.4 mmol). The solution was heated at reflux for 1.5 h and then cooled to rt. The solvent was removed in vacuo to give the crude product which was then filtered through a plug of silica gel, eluting with 1:1 EtOAc/hexanes containing 1% AcOH. Concentration of the filtrate afforded 0.70 g (97%) of a yellow liquid. IR (thin film): 3085, 2104, 1719, 1414, 1283, 1218 $cm^{-1}$. $^1H$ NMR (400 MHz, $CDCl_3$): δ3.95 (s, 2H), 9.82 (s, 1H). (Dyke et al. *J. Am. Chem. Soc.* 1997, 119, 6883) $^1H$ NMR (300 MHz, $CDCl_3$): δ4.0 (s, 2H), 10.3 (s, 1H). $^{13}C$ NMR (100

MHz, CDCl$_3$): δ50.0, 174.6. HRMS (CI) m/z 101.0226 (M+C$_2$H$_3$N$_3$O$_2$ requires 101.0225).

Synthesis of 3-Azidopropionic Acid (Compound 24)

To a solution of 3-bromopropionic acid (5.0 g, 33 mmol) in MeOH (20 mL) was added NaN$_3$ (2.3 g, 36 mmol). The solution was heated at reflux for 2 h and then cooled to rt. The solvent was removed in vacuo to give the crude product which was then filtered through a plug of silica gel, eluting with 1:1 EtOAc/hexanes containing 1% AcOH. Concentration of the filtrate afforded 3.1 g (82%) of a yellow liquid. IR (thin film): 3493, 2989, 2109, 1713 cm$^{-1}$. $^1$H NMR (400 MHz, CDCl$_3$): δ2.59 (t, 2H, J=6.4), 3.54 (t, 2H, J=6.4), 9.43 (s 1H). $^{13}$C NMR (100 MHz, CDCl$_3$): δ33.7, 46.4, 177.4. HRMS (CI) m/z 116.0465 (MH+C$_3$H$_6$N$_3$O$_2$ requires 116.0460).

Preparation of N-Benzyloxyacetylmannosamine (Mixture of Anomers) (31)

To a round-bottom flask containing sat. NaHCO$_3$ (9 mL) was added mannosamine hydrochloride (500 mg, 2.30 mmol). The solution was stirred for 1 h under N$_2$, at which point benzyloxyacetyl chloride (0.44 mL, 2.8 mmol) was added dropwise via syringe. The biphasic mixture was stirred vigorously for 4 h resulting in a clear light yellow solution. The solution was concentrated and the residue was purified by silica gel chromatography eluting with a gradient of 20:1 to 10:1 CHCl$_3$/MeOH to afford 512 mg (68%) of a viscous oil. IR (thin film): 3331, 2918, 2356, 1652, 1524 cm$^{-1}$. $^1$H NMR (400 MHz, D$_2$O): δ3.26 (s, 1H), 3.33 (app d, 1H, J=6.7), 3.45 (app t, 1H, J=9.7), 3.54–3.66 (m, 1H), 3.69 (app d, 1H, J=4.8), 3.72 (d, 1H, J=2.0), 3.74–3.86 (m, 2H), 3.98 (dd, 1H, J=4.5, 9.8), 4.06 (s, 2H), 4.10 (s, 1H), 4.24–4.27 (m, 1H), 4.38–4.40(m, 1H), 4.55 (s, 2H), 4.57 (d, 1H, J=4.3), 4.97 (s, 1H), 4.99 (s, 1H), 7.32–7.36 (m, 10H), 7.49 (d, 1H, J=10.7), 7.58 (d, 1H, J=9.6). $^{13}$C NMR (100 MHz, D$_2$O): δ52.9, 60.4, 66.8, 68.5, 68.7, 72.0, 73.5, 76.5, 89.3, 92.8, 128.5, 128.6, 128.7, 128.8. HRMS (FAB) m/z 328.1396 (MH+C$_{15}$H$_{22}$NO$_7$ requires 328.1396).

Preparation of 1,3,4,6-Tetra-O-acetyl-N-benzyloxyacetylmannosamine (Mixture of Anomers) (32)

A solution of 31 (512 mg, 1.56 mmol) in pyridine (5 mL) was cooled to 0° C. To this solution was added acetic anhydride (2.5 mL, 27 mmol) and a catalytic amount of DMAP. The reaction mixture was stirred overnight and allowed to warm to rt. The resulting light yellow solution was diluted with CH$_2$Cl$_2$ (100 mL) and washed with 1 N HCl (3×50 mL), sat. NaHCO$_3$ (2×50 mL), water (2×50 mL) and sat. NaCl (1×50 mL). The combined aqueous layers were back extracted with 50 mL of CH$_2$Cl$_2$. The combined organic layers were dried over Na$_2$SO$_4$ and concentrated. The crude product was purified by silica gel chromatography eluting with a gradient of 1:4 to 1:1 EtOAc/hexanes to afford 745 mg (96%) of a light yellow oil. IR (thin film): 3409, 2959, 2357, 1750, 1692, 1520 cm$^{-1}$. $^1$H NMR (300 MHz, CDCl$_3$): δ1.90 (s, 6H), 1.99 (s, 6H), 2.06 (s, 6H), 2.18 (s, 6H), 3.79–3.84 (m, 1H), 3.91–3.99 (m, 1H), 4.02 (d, 2H, J=2.8), 4.04–4.07 (m, 2H), 4.14 (dd, 2H, J=2.7, 17.8), 4.20 (dd, 1H, J=3.9, 9.1), 4.5 (app t, 1H, J=6.3), 4.60–4.65 (m, 4H), 4.66–4.68 (m, 1H), 4.79 (ddd, 1H, J=1.6, 3.8, 13.2), 5.07 (dd, 1H, J=3.9, 9.8), 5.19 (app t, 1H, J=4.7), 5.24 (app t, 1H, J=9.8), 5.35 (dd, 1H, J=4.2, 10.2), 5.90 (d, 1H, J=1.6), 6.03 (d, 1H, J=1.6), 6.89 (d, 1H, J=-9.6), 7.03 (d, 1H, J=9.3), 7.32–7.39 (m, 10H). $^{13}$C NMR (125 MHz, CDCl$_3$): δ20.3, 20.4, 20.6, 20.7, 20.8, 48.6, 61.7, 65.1, 65.2, 68.9, 69.1, 69.3, 70.2, 71.3, 73.3, 73.5, 73.6, 77.8, 97.1, 127.8, 127.9, 128.2, 128.3, 128.4, 128.6, 128.7, 136.4, 136.6, 169.4, 169.7, 170.1, 170.5. MS (FAB) m/z 496 (MH+). Anal. Calcd for C$_{23}$H$_{29}$NO$_{11}$: C, 55.75; H, 5.90; N, 2.83; Found: C, 55.54; H, 5.93; N, 2.68.

Preparation of N-Iodoacetylmannosamine (Mixture of Anomers) (33) (Scheme 9a)

To a solution of mannosamine hydrochloride (244 mg, 1.13 mmol) in dry MeOH (11 mL) was added 1 M sodium methoxide in MeOH (1.13 mL). The reaction mixture was stirred for 1 h at rt, followed by the addition of iodoacetic anhydride (1.0 g, 2.8 mmol). The resulting solution was stirred overnight at rt under an atmosphere of N$_2$. To this was added H$_2$O (5 mL) and the solution was stirred for an additional 1 h. The solution was neutralized with sat. NaHCO$_3$ and concentrated. The residue was filtered through a plug of silica gel eluting with 5:1 CHCl$_3$/MeOH. The crude product obtained was used in the next step without further purification. $^1$H NMR (300 MHz, D$_2$O): δ3.34–3.41 (m, 1H), 3.44–3.52 (m, 1H), 3.53–3.62 (m, 1H), 3.78 (d, 2H, J=1.0), 3.80 (d, 2H, J=1.3), 3.83 (br s, 2H), 4.00–4.07 (m, 1H), 4.24 (app d, 1H, J=4.6), 4.38 (app d, 1H, J=4.3), 4.84 (d, 1H J=1.6), 4.91 (d, 1H, J=1.4). $^{13}$C NMR (125 MHz, D$_2$O): δ48.8, 53.7, 60.3, 66.4, 66.7, 68.8, 71.9, 72.0, 76.3, 92.4, 92.9, 172.7, 176.1. MS (ES) m/z 370.09 (MNa+).

Preparation of N-Azidoacetylmannosamine (Mixture of Anomers) (20)

To a solution of 33 (392 mg, 1.13 mmol) in MeOH (2.3 mL) was added NaN$_3$ (734 mg, 11.3 mmol). The mixture was heated at reflux overnight and allowed to cool to rt and concentrated. The residue was filtered through a plug of silica gel eluting with 5:1 CHCl$_3$/MeOH. The crude product obtained was further purified by silica gel chromatography eluting with a slow gradient from 50:1 to 6:1 CHCl3/MeOH. The fractions collected were concentrated and redissolved in a minimum amount of water. Lyophilization afforded 271 mg (91% over two steps) of a white powder. IR (KBr pellet): 3463, 2126, 1624 cm$^{-1}$. $^1$H NMR (300 MHz, D$_2$O)): δ3.56 (app t, 2H, J=9.1), 3.65–3.72 (m, 1H), 3.77–3.83 (m, 1H), 3.85–3.87 (m, 2H), 3.89–3.91 (m, 2H), 3.94 (dd, 2H, J=2.3, 2.7), 3.99 (app d, 1H, J=3.1), 4.02 (app d, 1H, J=3.5), 4.15 (s, 4H), 5.23 (d, 1H, J=1.7), 5.28 (d, 1H, J=3.4). $^{13}$C NMR (125 MHz, D$_2$O): °51.5, 51.6, 53.2, 54.0, 54.2, 60.2, 66.4, 66.6, 68.7, 69.9, 70.5, 71.5, 71.9, 75.9, 76.3, 92.7, 92.8. HRMS (FAB) m/z 263.0991 (MH+C$_8$H$_{15}$N$_4$O$_6$ requires 263.0992).

Synthesis of N--azidoacetylmannosamine and Aceylated N-azidomannosamine (Scheme 9b)

A solution of mannosamine hydrochloride (250 mg, 1.16 mmol) and sodium methoxide (1.16 ml of a 1 M methanolic solution) in dry MeOH (10 ml) was stirred for 1 h at room temperature, after which chloroacetic anhydride (991 mg, 5.80 mmol) was added. The resulting solution was stirred overnight at room temperature under an atmosphere of N$_2$ and then quenched with H$_2$O (5 ml) for 1 hour. The solution was neutralized with saturated NaHCO3 and concentrated, and the residue was filtered through a plug of silica gel eluting with 5:1 CHCl$_{13}$/MeOH. The crude product obtained was dissolved in DMF (10 ml) and NaN$_3$ (78 mg, 1.39 mmol) was added. After heating at reflux overnight, the solution was cooled and concentrated. Purification by silica gel chromatography eluting with a gradient of 50:1 to 6:1 CHCl$_3$/MeOH afforded 179 mg of compound 20 (59% over two steps). The compound was peracetylated prior to incubation with cells as follows. A solution of 20 (25 mg, 0.095 mmol), acetic anhydride (1.0 ml, 11 mmol) and a catalytic amount of DMAP in pyridine (2 ml) was cooled to 0° C. The mixture was stirred overnight, warmed to rt, then diluted with CH$_2$Cl$_2$ (100 ml) and washed with 1 N HCl (3×50 ml), sat. NaHCO$_3$ (1×50 ml), water (1×50 ml) and saturated NaCl (1×50 ml). The combined organic layers were dried over Na$_2$SO$_4$ and concentrated. The crude product was purified by silica gel chromatography eluting with a gradient of 1:10 to 1:2 EtOAc/hexanes to afford 39 mg (95%) of acetylated 20 (compound 36).

Preparation of 1,3,4,6-Tetra-O-acetyl-N-acetylmannosamine (Mixture of Anomers) (35)

A solution of N-acetylmannosamine (100 mg, 0.420 mmol) in pyridine (5 mL) was stirred at 0° C. To this solution was added acetic anhydride (5.0 mL, 53 mmol) and a catalytic amount of DMAP. The mixture was stirred overnight and allowed to warm to rt. Concentration and co-evaporation with toluene (6×10 mL) afforded the crude product which was purified via silica gel chromatography eluting with a gradient of 1:4 to 1:1 EtOAc/hexanes, yielding 153 mg (94%) of a viscous oil. IR (thin film): 3368, 2965, 2255, 1750, 1665, 1536 cm$^{-1}$. $^1$H NMR (500 MHz, CDCl$_3$): δ2.05 (app s, 6H), 2.051 (app s, 6H), 2.08 (app s, 9H), 2.08 (s, 3H), 2.085 (s, 3H), 2.09 (s, 3H), 3.79 (ddd, 1H, J=2.5, 5.3, 9.6), 4.02–4.05 (m, 2H), 4.08 (dd, 1H, J=2.4, 12.4), 4.27 (dd, 1H, J=3.8, 5.5), 4.29 (dd, 1H, J=3.2, 5.5), 4.62 (ddd, 1H, J=1.8, 4.5, 9.2), 4.76 (dd, 1H, J=1.7, 4.0, 9.1), 5.04 (dd, 1H, J=4.0, 9.9), 5.11 (app t, 1H, J=9.7), 5.15 (app t, 1H, J=10.0), 5.32 (dd, 1H, J=4.5, 10.2), 5.84 (d, 1H, J=1.7), 5.92 (d, 1H, J=9.1), 6.00 (d, 1H, J=1.7), 6.01 (d, 1H, J=9.1). $^{13}$C NMR (125 MHz, CDCl$_3$): δ20.5, 20.6, 20.7, 20.8, 23.1, 23.3, 49.3, 49.5, 50.7, 61.9, 62.1, 65.3, 65.5, 68.8, 70.1, 71.3, 73.4, 76.7, 77.0, 77.2, 90.6, 91.7, 169.6, 169.7, 169.9, 170.0, 170.2, 170.5. HRMS (FAB) m/z 412.1227 (MNa+C$_{16}$H$_{23}$NNaO$_{10}$ requires 412.1220).

Preparation of 1,3,4,6-Tetra-O-acetyl-N-azidoacetylmannosamine (Mixture of Anomers) (36)

A solution of 20 (25 mg, 0.095 mmol) in pyridine (2 mL) was cooled to 0° C. To this solution was added acetic anhydride (1.0 ml, 11 mmol) and a catalytic amount of DMAP. The reaction mixture was stirred overnight and allowed to warm to rt. The resulting light yellow solution was diluted with CH$_2$Cl$_2$ (100 mL) and washed with 1 N HCl (3×50 mL), sat. NaHCO$_3$ (1×50 mL), water (1×50 mL) and sat. NaCl (1×50 mL). The combined aqueous layers were back extracted with 50 mL of CH$_2$Cl$_2$. The combined organic layers were dried over Na$_2$SO$_4$ and concentrated. The crude product was purified by silica gel chromatography eluting with a gradient of 1:10 to 1:2 EtOAc/hexanes to afford 39 mg (95%) of a light yellow oil. IR (thin film): 3317, 2106, 1744, 1677, 1529 cm$^{-1}$. $^1$H NMR (500 MHz, CDCl$^3$): δ2.05 (app s, 6H), 2.10 (s, 3H), 2.12 (s, 3H), 3.82 (ddd, 1H, J=2.4, 4.5, 9.6), 3.93 (s, 2H), 4.13 (dd, 1H, J=2.4, 12.6), 4.29 (dd, 1H, J=4.5, 12.6), 5.15 (app t, 1H, J=9.6), 5.21 (app t, 1H, J=5.7), 5.78 (app t, 1H, J=4.5), 6.37 (d, 1H, J=5.7). $^{13}$C NMR (125 MHz, CDCl$_3$): δ20.5, 20.5, 20.6, 20.6, 20.6, 20.8, 20.8, 51.2, 52.4, 52.5, 53.2, 61.4, 61.5, 67.4, 67.6, 69.8, 70.3, 72.0, 72.1, 72.9, 90.2, 92.1, 166.9, 168.6, 169.1, 169.2, 170.6, 170.8, 171.5. HRMS (FAB) m/z 437.1496 (MLi+C$_{16}$H$_{22}$LiN$_4$O$_{10}$ requires 437.1496).

Synthesis of 2-chloro-4-nitromethylbenzoate (40)

To a stirred solution of 2-chloro-4-nitrobenzoic acid (9.35 g, 46.0 mmol) in CH$_2$Cl$_2$ (170 mL) at 0° C. was added MeOH (2.0 mL, 51 mmol) and a catalytic amount of DMAP. To this solution was added 1-(3-dimethylaminopropyl)-3-ethylcarbodiimide (EDC) (9.78 g, 51.0 mmol) and the mixture was stirred at 0° C. for an additional 2 h before warming to rt overnight. The reaction mixture was poured into a separatory funnel and washed successively with sat. NaHCO$_3$ (3×50 mL), water (2×50 mL) and sat. NaCl (2×50 mL). The combined aqueous layers were back extracted with 50 mL of CH$_2$Cl$_2$. The combined organic layers were dried over Na$_2$SO$_4$ and concentrated. The crude product was purified by silica gel chromatography eluting with 1:4 EtOAc/hexanes to afford 6.7 g (67%) of a light yellow solid, mp 71–72° C. IR (thin film): 3429, 3100, 3040, 2965, 2875, 1954, 1720 cm$^{-1}$. $^1$H NMR (300 MHz, CDCl$_3$): δ3.98 (s, 3 H), 7.97 (d, 1 H, J=8.6), 8.16 (dd, 1 H, J=2.2, 8.5), 8.32 (d, 1 H, J=2.2). $^{13}$C NMR (125 MHz, CDCl$_3$): δ53.0, 121.4, 125.9, 132.0, 134.8, 135.7, 164.6. MS (FAB) m/z 216.0. Anal. Calcd for C$_8$H$_6$ClNO$_4$: C, 44.57; H, 2.81; N, 6.50; Found: C, 44.37; H, 2.78; N, 6.88.

Synthesis of 1-methyl-2-iodoterephthalate (44)

To a round-bottom flask charged with 5 mL of cold conc. HCl was added 1-methyl-2-aminoterephthalate (500 mg, 2.56 mmol). A solution of NaNO$_2$ (180 mg, 2.64 mmol) in 1 mL of H$_2$O was added dropwise, resulting in the evolution of a small amount of orange gas. The mixture was stirred for 30 min at rt and then filtered through glass wool into a solution of KI (4.30 g, 25.0 mmol) in 7 mL of H$_2$O. The dark red solution was stirred for 1 h and then diluted with CH$_2$Cl$_2$ (100 mL) and washed with sat. Na$_2$SO$_3$ (2×10 mL). The organic layer was washed with water (2×20 mL) and sat. NaCl (1×20 mL). The combined aqueous layers were back extracted with CH$_2$Cl$_2$ (20 mL). The combined organic layers were dried over Na$_2$SO$_4$ and concentrated. The crude product was dissolved in a minimum amount of MeOH and H$_2$O was added until the solution appeared slightly cloudy. Cooling to 4° C. and subsequent filtration afforded 449 mg (57%) of a bright yellow solid, mp 155–157° C. IR (thin film): 2956, 2893, 2823, 2658, 2525, 1733, 1695, 1549 cm$^{-1}$. $^1$H NMR (300 MHz, CDCl$_3$): δ3.97 (s, 3H), 7.84 (d, 1H, J=8.1), 8.12 (dd, 1H, J=1.7, 8.1), 8.69 (d, 1H, J=1.5). $^{13}$C NMR (125 MHz, CDCl$_3$): δ50.6, 129.4, 130.5, 132.3, 140.1, 142.5, 166.5, 168.6, 227.5. MS (CI) m/z 306 (M+). Anal. Calcd for C$_9$H$_7$IO$_4$: C, 35.32; H, 2.31; Found: C, 35.67; H, 2.21.

Synthesis of Compound 45

To a flame dried flask was added dry MeOH (3 mL), TEA (0.3 mL, 2 mmol), compound 44 (300 mg, 1.00 mmol) and palladium acetate (2.2 mg, 0.010 mmol). The mixture was degassed in vacuo. While stirring under an atmosphere of Ar, diphenylphosphine (0.17 mL, 1.0 mmol) was added to the flask via syringe. The resulting solution was heated at reflux overnight, and then allowed to cool to rt and concentrated. The residue was dissolved in 250 mL of a 1:1 mixture of CH$_2$Cl$_2$/H$_2$O and the layers were separated. The organic layer was washed with 1 N HCl (1×10 mL) and concentrated. The crude product was dissolved in a minimum amount of methanol and an equal amount of H$_2$O was added. The solution was cooled to 4° C for 2 h and the resulting solid was collected by filtration. The pure product was isolated as 245 mg (69%) of a golden yellow solid, mp 183–185° C. IR (thin film): 3051, 3001, 2950, 2608, 2481, 1720, 1587, 1562 cm$^{-1}$. $^1$H NMR (400MHz, CDCl$_3$): δ3.75 (s, 3H), 7.28–7.35 (m, 11H), 7.63–7.67 (m, 1H), 8.04–8.07 (m, 1H). $^{13}$C NMR (125 MHz, CDCl$_3$): δ52.4, 128.5, 128.6, 128.7, 129.0, 129.7, 130.6, 131.0, 131.8, 131.9, 133.7, 133.9, 135.4, 136.8, 152.7, 169.7, 221.9. $^{31}$P NMR (160 MHz, CDCl$_3$): δ-3.67. MS (FAB) m/z 365.1 (MH+).

Synthesis of Diphenylphosphanylmethanol (53) (Slany et al. *Tetrahedron Lett*. 1996, 37, 9053)

To a round-bottom flask charged with paraformaldehyde (0.52 g, 17 mmol) under an atmosphere of Ar was added diphenylphosphine (3.1 mL, 18 mmol) via syringe. The mixture was heated to 120° C. for 90 min and then cooled to rt. The crude product was diluted with CHCl$_3$ (15 mL) and the remaining solid paraformaldehyde was filtered off. Concentration afforded 3.8 g (98%) of a clear, highly viscous oil. IR (thin film): 3330, 3503, 2889, 2836, 1962, 1892, 1817, 1586 cm$^{-1}$. $^1$H NMR (300 MHz, CDCl$_3$): 2.35 (s, 1H), 4.37

(d, 2H, J=7.5), 7.36–7.38 (m, 5H), 7.48–7.51 (m, 5H). (Muller et al. *J. Organomet. Chem.* 1995, 495, 103)) $^1$H NMR (300 MHz, $CD_2Cl_2$): δ2.5 (br s, 1H), 4.3 (d, 2H, J=7.9), 7.2–7.4 (m, 10H). $^{13}$C NMR (100 MHz, $CDCl_3$): δ62.6, 62.8, 128.6, 128.7, 129.0, 131.4, 131.5, 133.1, 133.3, 135.5, 135.6. $^{31}$P NMR (160 MHz, $CDCl_3$): δ-10.24. HRMS (CI) m/z 216.0697 ($M+C_{13}H_{13}OP$ requires 216.0704).

Synthesis of Compound 55

To a stirred solution of N-9-fluorenylmethoxycarbonyl-L-alanine (311 mg, 1.00 mmol) in $CH_2Cl_2$ (4 mL) at 0° C. was added 53 (365 mg, 1.69 mmol) and a catalytic amount of DMAP. To this solution was added EDC (219 mg, 1.14 mmol) and the mixture was stirred at 0° C. for an additional 2 h before warming to rt overnight. The reaction mixture was poured into a separatory funnel and washed successively with sat. $NaHCO_3$ (2×20 mL), water (2×20 mL) and sat. NaCl (2×20 mL). The combined aqueous layers were back extracted with 30 mL of $CH_2Cl_2$. The combined organic layers were dried over $Na_2SO_4$ and concentrated. The crude product was purified by silica gel chromatography eluting with a gradient of 1:10 to 1:4 EtOAc/hexanes to afford 232 mg (46%) of a white waxy solid. IR (thin film): 3330, 3055, 2984, 2942, 2249, 1955, 1722, 1530 $cm^{-1}$. $^1$H NMR (300 MHz, $CDCl_3$): δ1.25 (d, 3H, J=7.1), 4.20 (t, 1H, J=7.1), 4.37 (d, 2H, J=7.1), 4.84 (dd, 1H, J=6.2, 13.0), 4.99 (dd, 1H, J=6.6, 13.0), 5.23 (d, 1H, J=7.8), 7.29–7.49 (m, 14H), 7.58 (d, 2H, J=7.3),7.77 (d, 2H, J=7.5). $^{13}$C NMR (125 MHz, $CDCl_3$: δ18.6, 47.1, 49.6, 64.2, 64.3, 66.9, 119.9, 125.0, 127.0, 127.6, 127.7, 128.5, 128.6, 128.7, 128.8, 129.1, 129.3, 131.3, 131.4, 132.8, 132.9, 133.1, 133.3, 141.3, 143.7, 155.5, 172.8. $^{31}$P NMR (160 MHz, $CDCl_3$): δ-15.21. HRMS (FAB) m/a 526.1785 ($MH+C_{31}H_{29}NO_5P$ requires 526.1783) Due to the air sensitive nature of the product, oxidation occurred during analysis. The value reported for m/z is the phosphine oxide of 55.

Synthesis of (Diphenylphosphanyl)Methyl Acetate (56)

A solution of 53 (0.87 g, 4.0 mmol) in pyridine (10 mL) was cooled to 0° C. To this solution was added acetic anhydride (5.0 mL, 54 mmol) and a catalytic amount of DMAP. The reaction mixture was allowed to warm to rt while stirring overnight. The resulting light yellow solution was concentrated and co-evaporated with toluene (5×10 mL). The crude product was purified by silica gel chromatography eluting with 1:4 ethyl acetate/hexanes to afford 0.47 g (46%) of a light yellow oil. (The low yield of this reaction was determined to be due to the instability of the product during silica gel chromatography.) IR (thin film): 3053, 2926, 1744, 1481, 1434 $cm^{-1}$. $^1$H NMR (300 MHz, $CDCl_3$): δ2.02 (s, 3H), 4.85 (dd, 2H, J=1.9, 5.6), 7.35–7.39 (m, 5H), 7.45–7.50 (m, 5H). $^{13}$C NMR (100 MHz, $CDCl_3$): δ20.8, 63.5, 36.7, 128.6, 128.7, 129.2, 133.0, 133.2, 135.3, 135.4, 170.8. $^{31}$P NMR (160 MHz, $CDCl_3$): δ-16.17. HRMS (CI) m/z 259.0891 ($MH+C_{15}H_{16}O_2P$ requires 259.0888).

Synthesis of Methyl Azidoacetate (57)

To a solution of methyl bromoacetate (0.65 mL, 7.0 mmol) in $CH_3CN$ (7 mL) was added tetrabutylammonium azide (3.0 g, 10 mmol). The solution was heated at reflux overnight and then allowed to cool to rt. The solvent was removed in vacuo and the crude product was purified by silica gel chromatography eluting with 1:4 EtOAc/hexanes to afford 0.59 g (74%) of a clear liquid. IR (thin film): 3389, 2981, 2880, 2104, 1742 $cm^{-1}$. $^1$H NMR (500 MHz, $CDCl_3$): δ3.79 (s, 3H), 3.87 (s, 2H). $^{13}$C NMR (125 MHz, $CDCl_3$): δ50.2, 52.5, 168.7. HRMS (Submitted).

Treatment of Cells with Mannosamine Derivatives.

Cultures of Jurkat cells were seeded at a density of 1.25×10$^5$ cells/mL into 12-well tissue culture plates in a total volume of 2 mL of culture media. The appropriate amount of each sugar (1, 3, 20, 36, 37) in a solution of PBS was added and the cells were incubated for 3 d. Control wells containing no added sugar were also seeded with cells and incubated.

Propidium Iodide Assay

After growth in the presence of the appropriate sugars, cells were pelleted (3000×g, 2 min), washed twice with 1 mL avidin staining buffer (0.1% $NaN_3$, 0.1% FBS in PBS, pH=7.4) and diluted to a volume of 300 μL. Immediately prior to flow cytometry analysis, 10 μL of propidium iodide solution (1 mM in PBS) was added to each sample.

Labeling Procedures

After growth in the presence of the appropriate sugars, cells were pelleted (3000×g, 2 min), washed twice with 1 mL biotin staining buffer (0.1% FBS in PBS, pH=6.5) and diluted to a volume of 400 μL. Samples were suspended and added to 100 μL of biotin hydrazide solution (5 mM in PBS, pH=6.5). After incubation at rt for 1.5 h, the cells were pelleted (3 000×g, 2 min) and washed twice with avidin staining buffer. Cells were then suspended in 100 μL of avidin staining buffer and transferred into tubes containing 100 μL of FITC-avidin staining solution (4 μL FITC-avidin, 996 μL avidin staining buffer). After a 10 min incubation in the dark at 4° C., the cells were washed with 1 mL avidin staining buffer and the avidin staining process was repeated. The cells were pelleted (3000×g, 1 min) and washed twice with avidin staining buffer. The cells were then diluted to a volume of 300 μL for flow cytometry analysis.

EXAMPLE 1

Development of an Aqueous Staudinger Ligation and Water Soluble Azide

Two routes were devised to effect an aqueous Staudinger ligation, each incorporating several of the desired features. The first is shown in route A in Scheme 1. This reaction is known to proceed in high yield in wet ether (0.01% $H_2O$) (Keogh et al. *J. Org. Chem.* 1986, 51, 2767), however it was unknown whether hydrolysis of the aza-ylide (route B) would begin to compete in conditions approaching 55M $H_2O$.

Scheme 1

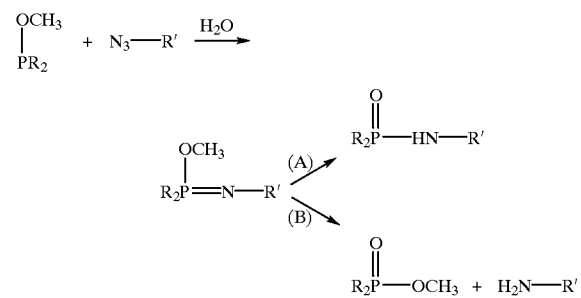

To address this issue, the water soluble azide 6 was synthesized according to Scheme 2. Commercially available tetraethylene glycol 5 was reacted with MsCl followed by displacement with $NaN_3$ to form the monoazide 6, which was then subjected to a reaction with a model phosphinite, methyl diphenylphosphinite 7, to afford phosphoramidate 8 (Scheme 2). THF was required as a co-solvent in order to solubilize compound 7, however the reaction continued to proceed with average yields of 91% at 10, 20, 30 and even 50% water. Reduction of 6 to the corresponding amine was not observed in any of these reactions, indicating that hydrolysis is not a significant side reaction. These test reactions were carried out at a concentration of 90 mM for both reactants and appeared by TLC analysis to go to completion in under two hours. This is an important feature of the reaction since biological conditions mandate that reactions take place at concentrations at or below the mM range. This reaction appeared promising since it takes place rapidly in water at relatively low concentrations of reactants and in high yield. However, the aryl substituents of phosphinite 7, are not readily derivatized, limiting the synthetic accessibility of functionalized water soluble derivatives. In addition, phosphinites are not particularly stable to oxidation (Corbridge *Phosphorus: an Outline of its Chemistry, Biochemistry and Technology;* 4th ed.; Elsevier: Amsterdam, 1990).

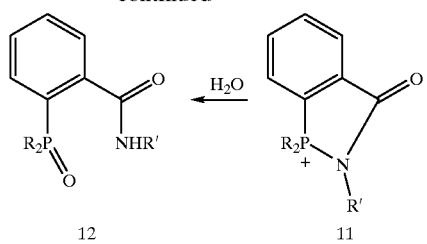

This reaction has the advantage of utilizing a more air stable class of phosphines that can be synthesized via a more general route. A model phosphine (13, Scheme 4) was synthesized via a palladium coupling reaction of diphenylphosphine (14) and an aryliodide 15 (Stelzer et al. *J.*

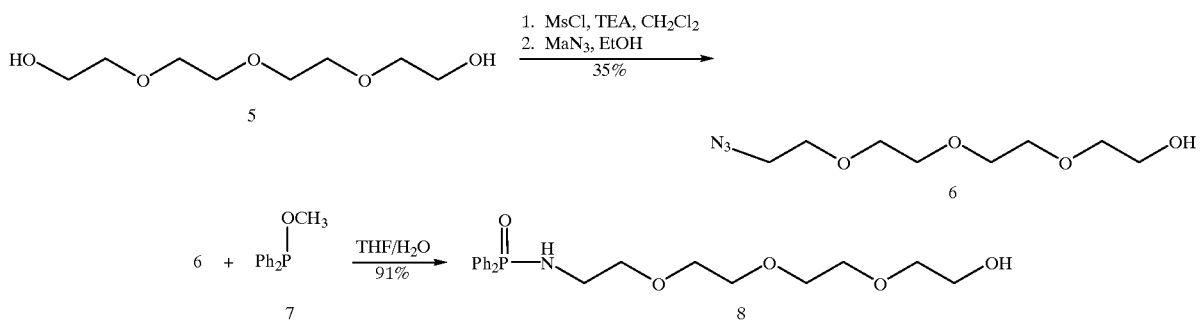

EXAMPLE 2

Synthesis of Phosphine Moiety with Methyl Ester as Covalent Trap for Aza-Ylide and Coupling to Carbohydrate Azides The disadvantages noted in Example 1 prompted the development of a second method, one that has not been previously reported, for effecting an aqueous Staudinger ligation (Scheme 3). We hypothesized that a methyl ester within the phosphine moiety 9 would provide a covalent trap for the aza-ylide 10. Subsequent rapid hydrolysis of the rearrangement product 11 yields the ligation product 12. Similar to the chemistry utilized by Kent and coworkers for native chemical ligation, this reaction involves a rapid cyclization via a five membered ring transition state, followed by an irreversible step to form the final product.

*Organomet. Chem.* 1996, 522, 69). The scheme is compatible with diverse functionality ideal for the construction of derivatized, water soluble phosphines.

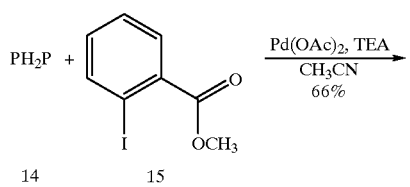

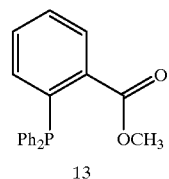

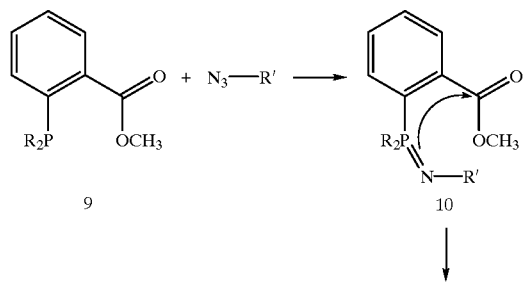

Phosphine 13 was reacted with carbohydrate azides 16 and 17 as shown in Scheme 5. Once again, a co-solvent was required to solubilize the model compounds.

Scheme 5

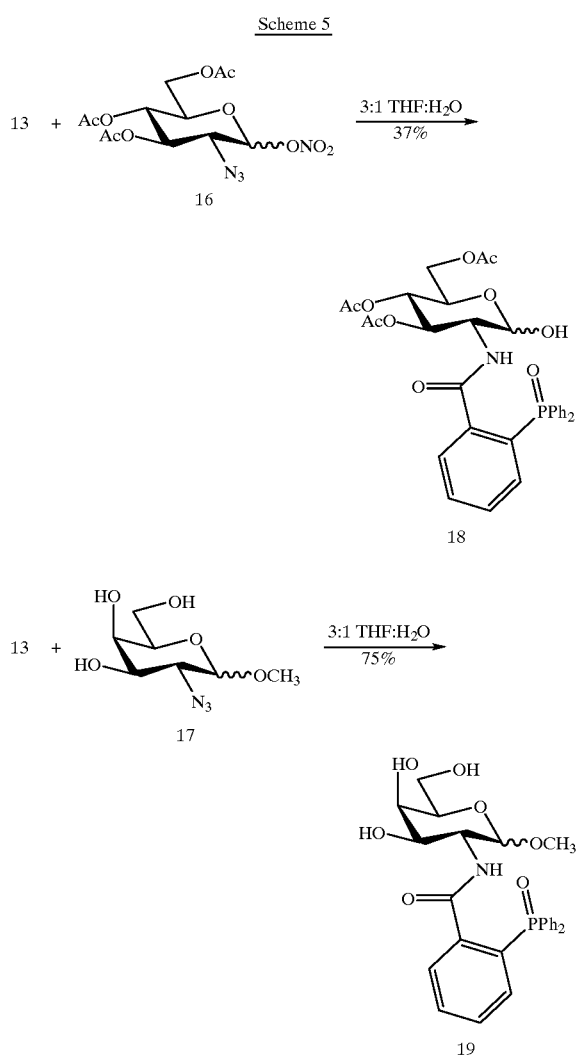

Phosphine 13 was successfully coupled to 16 to produce 18 at a range of concentrations of each reactant (1–50 mM). The reaction was complicated by the presence of the nitro group which cross-reacted with 13, reducing the yield of the desired product 18. However, no amine was observed, indicating that rearrangement to the amide is faster than aza-ylide hydrolysis. Furthermore, 18 was formed even when the concentration of each reactant was reduced to 1 mM. The reaction was also performed in a more polar solvent mixture (DMF/H$_2$O) to more accurately mimic a biological medium. Increasing the polarity of the solvent caused an apparent increase in the rate of the reaction.

A second azide substrate 17, without a nitro group, was coupled to 13 to produce 19 with a more satisfactory isolated yield (75%). On a qualitative level, these results indicate that the reaction will succeed at biologically relevant concentrations. Once a fully water soluble phosphine is synthesized, the reaction kinetics can be studied more quantitatively using IR to monitor disappearance of the azide, and $^{31}$P NMR to monitor oxidation of the phosphine.

EXAMPLE 3

Synthesis of Substrate for Use in Production of Azides within Cell Surface Sialic Acid Residues Having shown that the Staudinger ligation used to form 18 and 19 in Scheme 5 above has the potential to succeed in an aqueous environment, the next step was to synthesize a vehicle for the expression of azides within cell surface sialic acid residues. Azides were chosen as the cell surface coupling partner rather than phosphines due to their inherent stability and also due to size restrictions on the N-acyl substituents of mannosamine imposed by the enzymes of the sialic acid biosynthetic pathway (Jacobs et al. *Meth. Enzymol.* 1999, 303,:468–79). Two synthetic targets were designed: N-azidoacetylmannosamine 20 and N-azidopropanoylmannosamine 21. These compounds can be synthesized from mannosamine (22) and the corresponding haloacids (see schematic below).

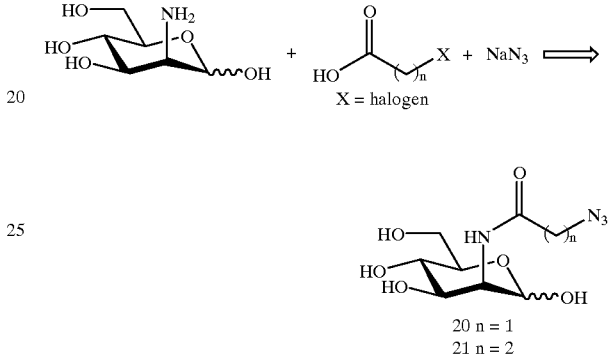

The azido-acids 23 and 24 were obtained in good yield by nucleophilic displacement of the corresponding bromides 25 and 26 (Scheme 6).

Scheme 6

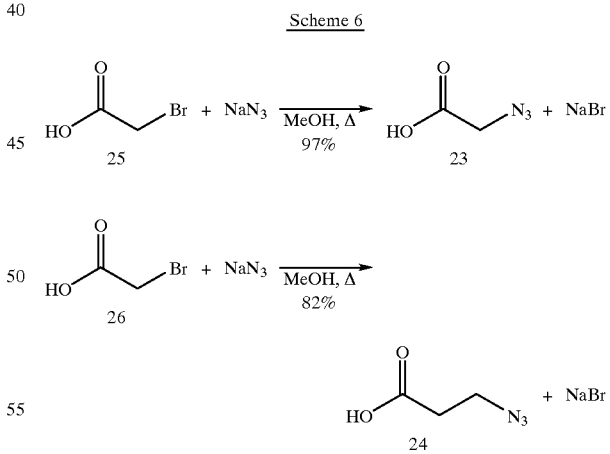

Compounds 25 and 26 were converted to the corresponding isobutyl carbonic anhydrides 27 and 28 as shown in Scheme 7, but the coupling reaction with mannosamine hydrochloride (29) produced only a complicated mixture of side products using either TEA or NaOMe to neutralize the starting material.

Scheme 7

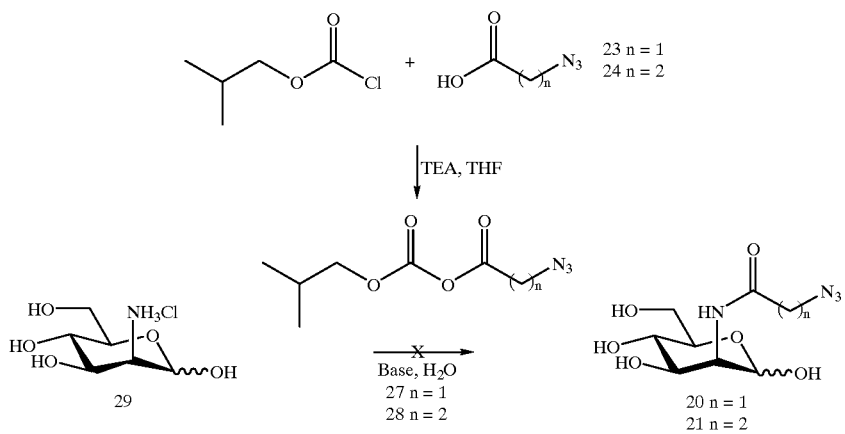

Repeated attempts to couple the azido-acids using a variety of amide bond coupling reagents were also unsuccessful.

An alternative route to 20 was pursued as shown in Scheme 8 below. Mannosamine hydrochloride (29) was acylated with benzyloxyacetyl chloride (30) to afford 31 which was acetylated to give 32.

Scheme 8

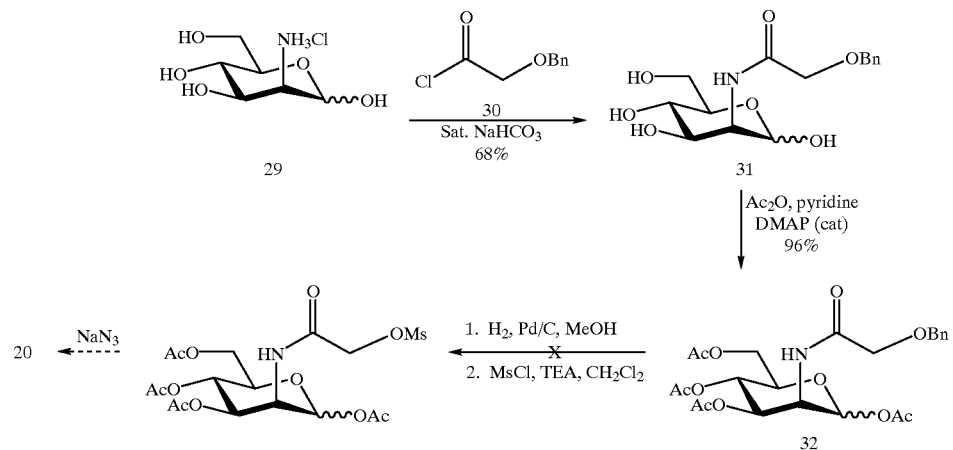

Unfortunately, attempts to deprotect the benzyl ether were accompanied by acetate migration to give a mixture of products, and such could not be avoided.

Figure 12:
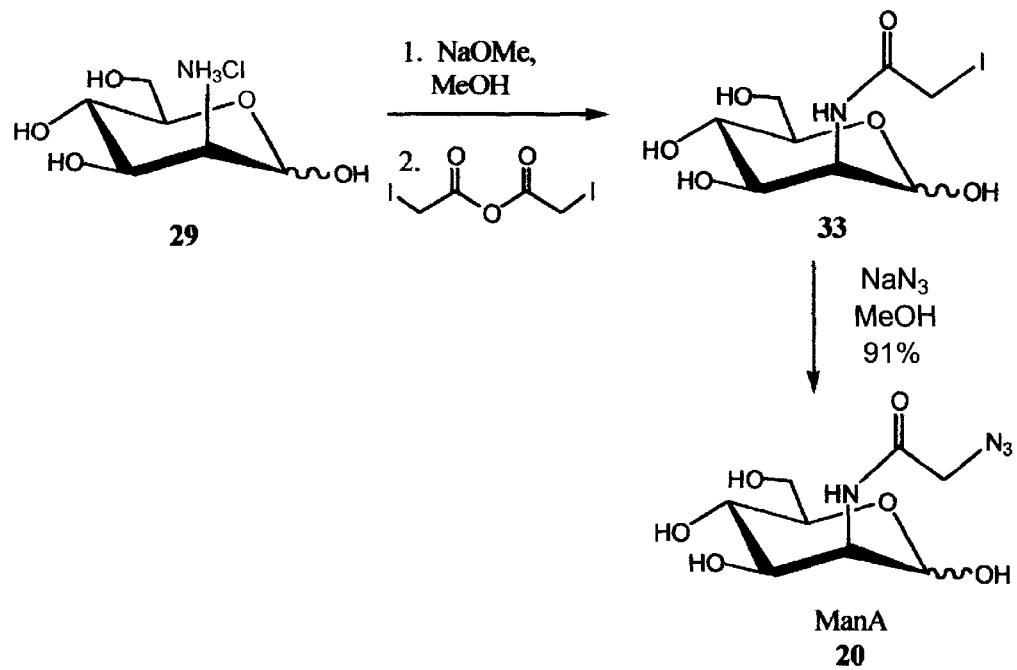
FIG. 12 is a schematic showing synthesis of a substrate for use in production of azides within cell surface sialic acid residues.
Figure 12:
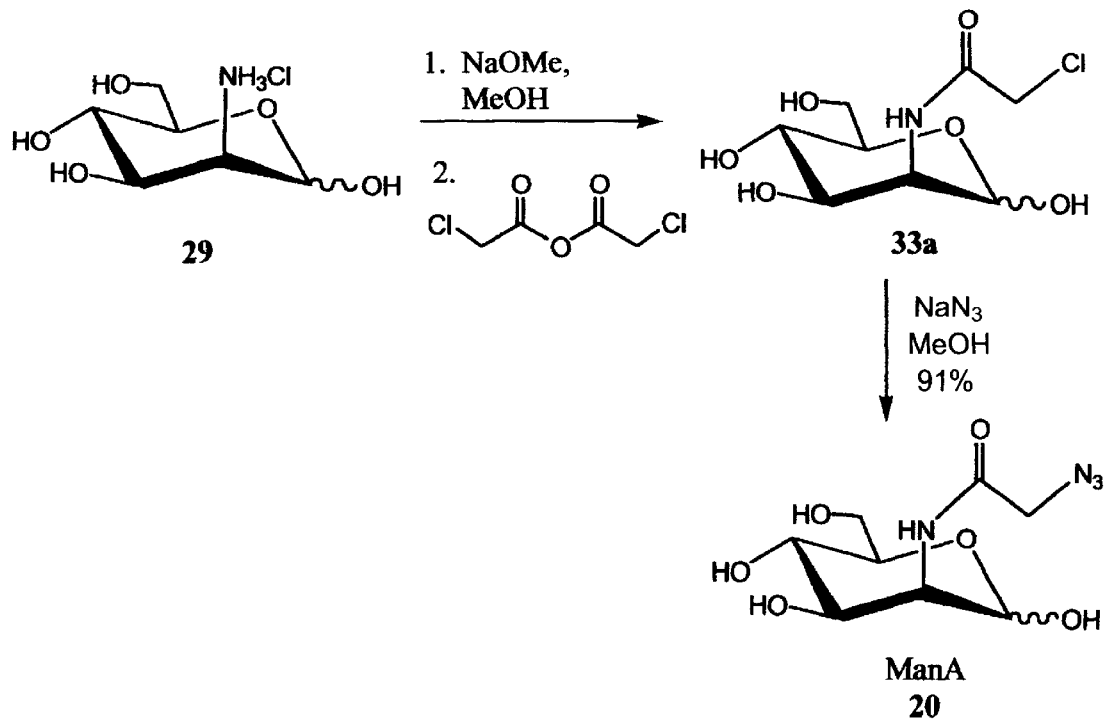
Figure 13:
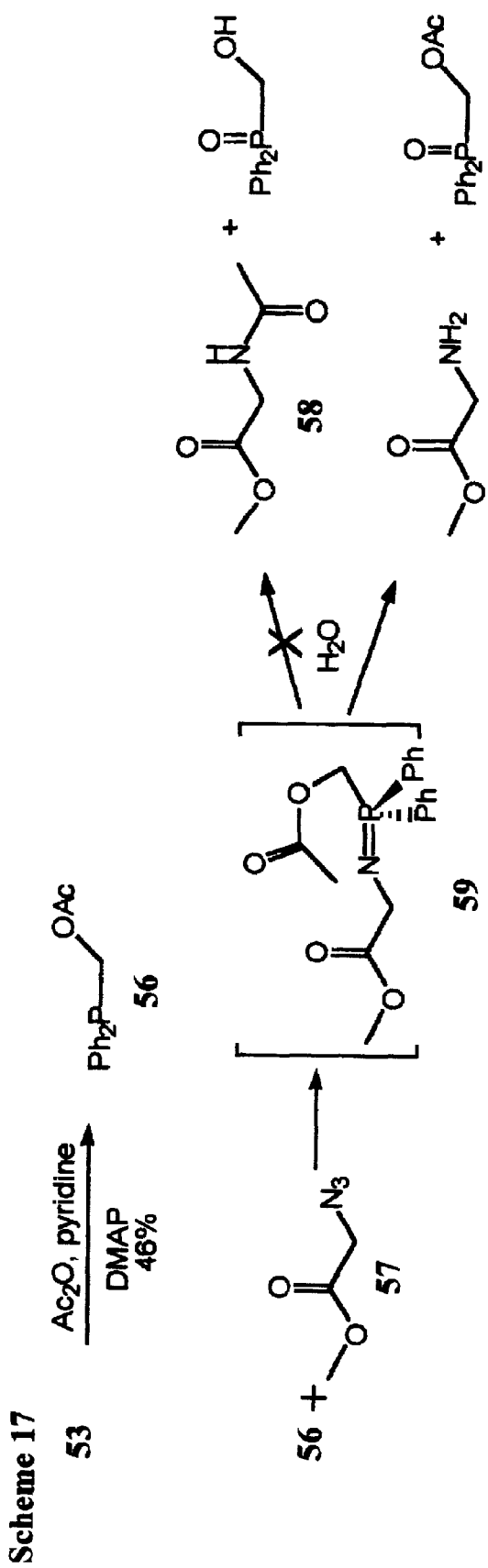
FIG. 13 is a schematic showing synthesis of an acetylated analog.

A successful scheme was devised based on a method used by Lu et al. *Carbohydr Res.* 1997, 303(3), 283–91 for the synthesis of N-iodoacetyl oligosaccharides. As shown in Schemes 9a and 9b (FIG. 12), 29 was neutralized with $NaOCH_3$ and then acylated with haloacetic anyhydride (e.g., iodoacetic anhydride in Scheme 9a or chloroacetic anyhydride in Scheme 9b) to give 33. Displacement with $NaN_3$ afforded the desired product ManAz (20).

EXAMPLE 4
Biocompatibility of ManAz Target Substrate

With the first of the two target substrates in hand, ManAz was evaluated for possible growth inhibition, toxicity, and metabolic incorporation into cell surface glycoconjugates (34, Scheme 10).

Scheme 10

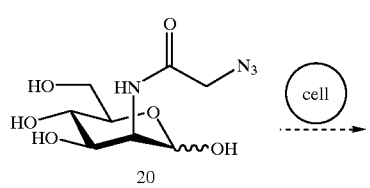

-continued

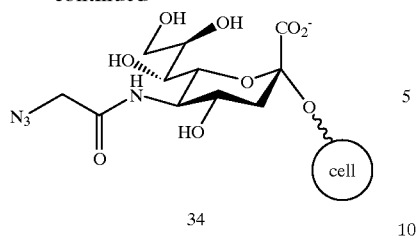

34

Toxicity was ascertained by incubating Jurkat cells, a human T-cell lymphoma cell line, with ManAz for three days at a range of concentrations, using the natural substrate ManNAc (1) as a negative control. Each experiment was performed in triplicate. The cells were counted to determine whether addition of 20 was inhibiting cell growth.

Figure 2:
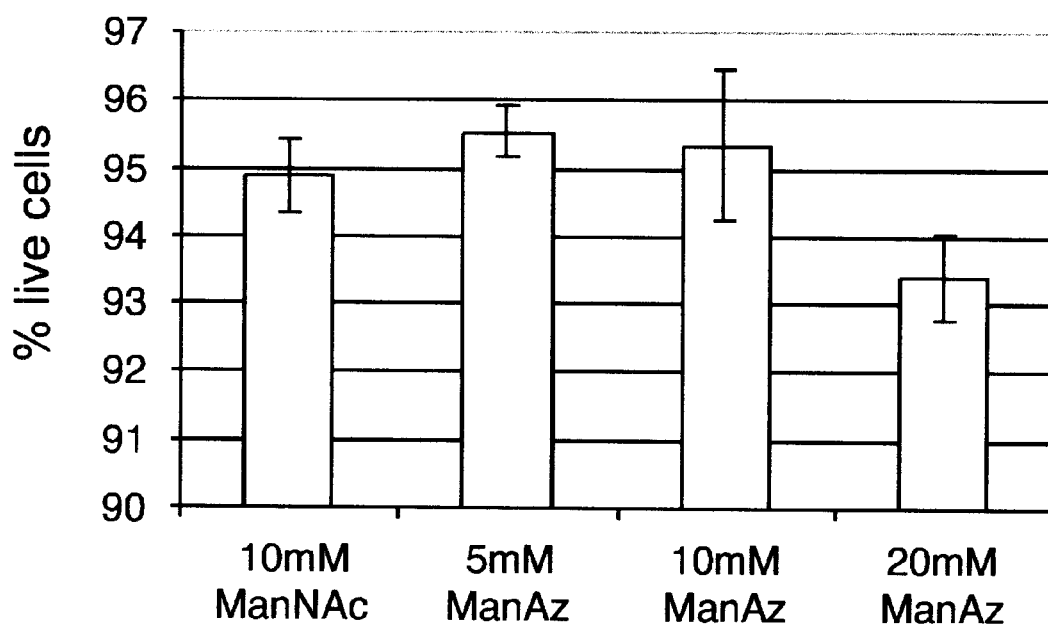
FIG. 2 is a graph showing the effect of ManAz on Jurkat cell viability. Error bars represent the standard deviation of the mean for three experiments.

As shown in FIG. 1, the addition of ManAz caused a decrease in the number of cells observed after 3 days of growth in a dose-dependent fashion. The cells were then treated with propidium iodide and analyzed by flow cytometry to determine the percentage of viable cells (FIG. 2). No significant change in the percentage of viable cells was observed. Thus, it appears that at the concentrations used, ManAz suppresses cell growth to a small degree, but does not kill the cells. The suppression of cell growth might reflect partial inhibition of glycoprotein synthesis at high concentrations, an effect we have observed with other mannosamine analogs.

EXAMPLE 5

Assay for Conversion of ManLev to SiaLev

Several assays have been developed for quantifying the conversion of ManLev to SiaLev on cell surface glycoconjugates (Yarema et al. *J. Biol. Chem.* 1998, 273, 31168). One of the most direct methods for detection of cell surface ketones is the two stage detection of the ketone with biotin hydrazide followed by FITC-Avidin, which can be detected by flow cytometry (illustrated below).

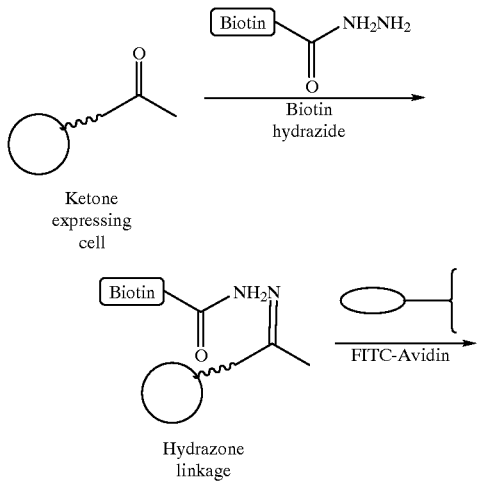

-continued

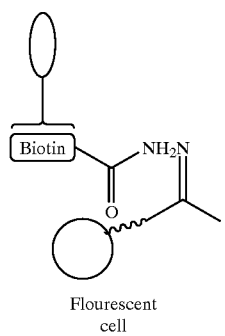

This assay can be used to obtain indirect evidence that ManAz is metabolized by the cells. If ManAz and ManLev compete for the same biosynthetic pathway, then increasing the ratio of ManAz to ManLev in the cell culture media should decrease the relative number of ketones expressed on the cell surface. This should result in a dose-dependent decrease in the fluorescence signal from ketone labeling.

Jurkat cells were incubated for three days with the appropriate amount of ManLev and ManAz (produced by the synthesis of Scheme 9a), or with media only as a control (no sugar). In order to eliminate the possibility that ManAz is not taken up by cells (Jacobs et al. *Meth. Enzymol.* 1999, 303, 468–79), the acetylated version was synthesized as shown in Scheme 11 (Khoukhi et al. *Tetrahedron Lett.* 1986, 27, 103 1). Acetylated monosaccharides are metabolized 200-fold more efficiently than the free sugars due to improved cellular uptake, which is followed by deacetylation by cytosolic esterases (Sarkar et al. 1995 *Proc. Natl. Acad. Sci. U.S.A.* 92, 3323 and Lemieux et al. 1999 *J. Am. Chem. Soc.* 121, 4278). In addition, lower concentrations of acetylated derivatives can be used, conserving material.

Scheme 11

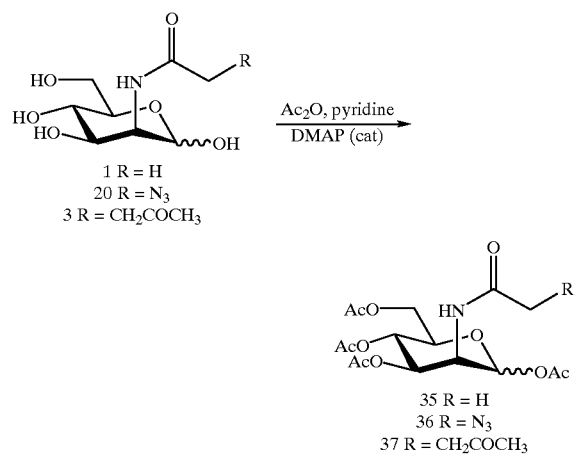

Figure 3:
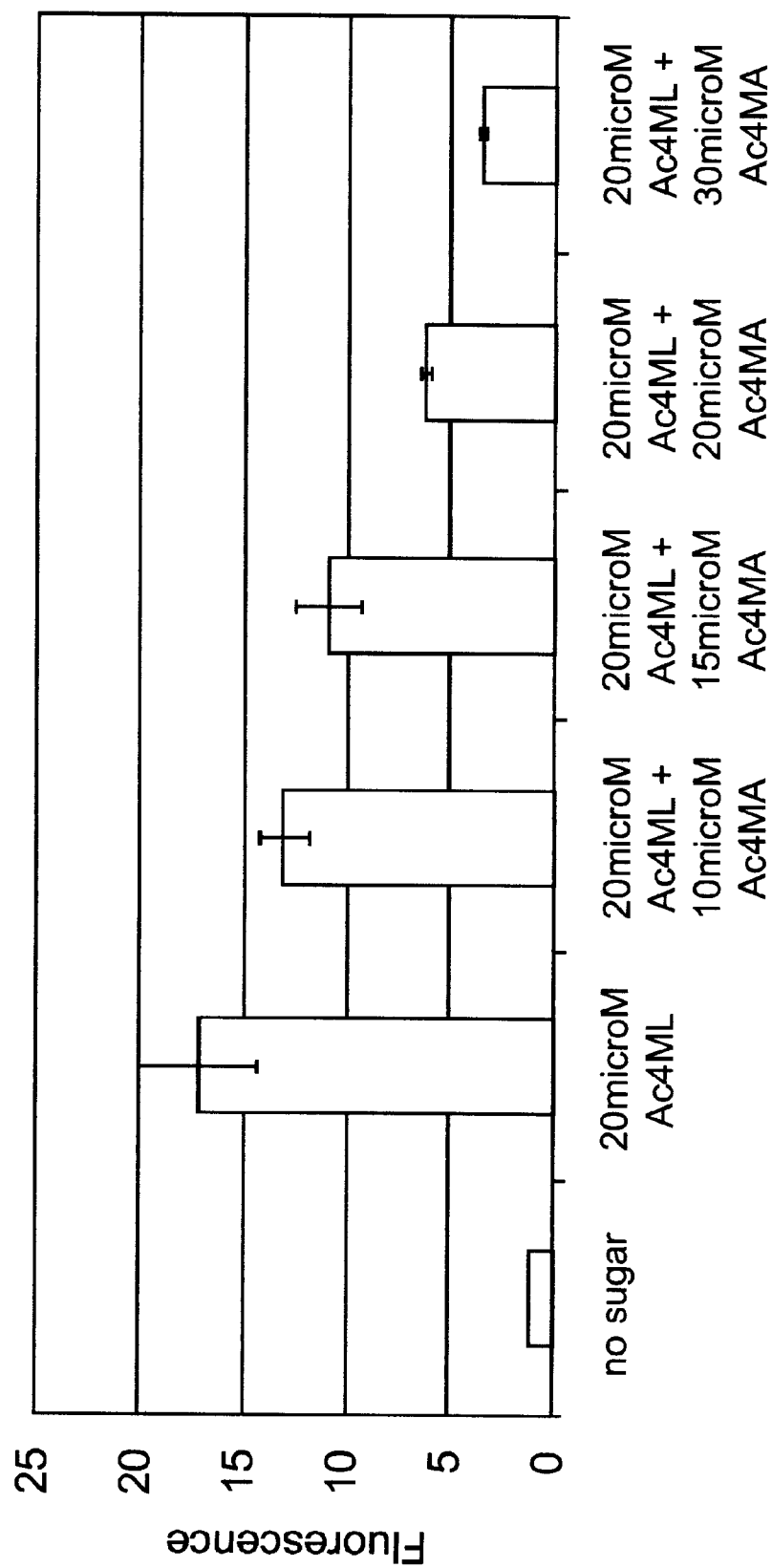
FIG. 3 is a graph showing the effect of ManAz on the metabolism of ManLev and subsequent ketone expression. No sugar served as a control. Ac4ML=acetylated ManLev; Ac4MA=acetylated ManAz. Error bars represent the standard deviation of the mean of the relative fluorescent intensities for two experiments.

The acetylated form of ManAz (36) was assessed for the ability to compete with acetylated ManLev (37). As shown in FIG. 3, increasing concentrations of acetylated ManAz (Ac4MA) resulted in proportionately decreasing fluorescence, indicating competition with ManLev (Ac4ML).

EXAMPLE 6

Assay for Cell Surface Azides Using Phosphine Having Biotin Attachment Site

In order to develop a more direct assay for cell surface azides, a phosphine is needed that has all of the features previously described, as well as a site of attachment for biotin (38, synthesis shown in schematic below).

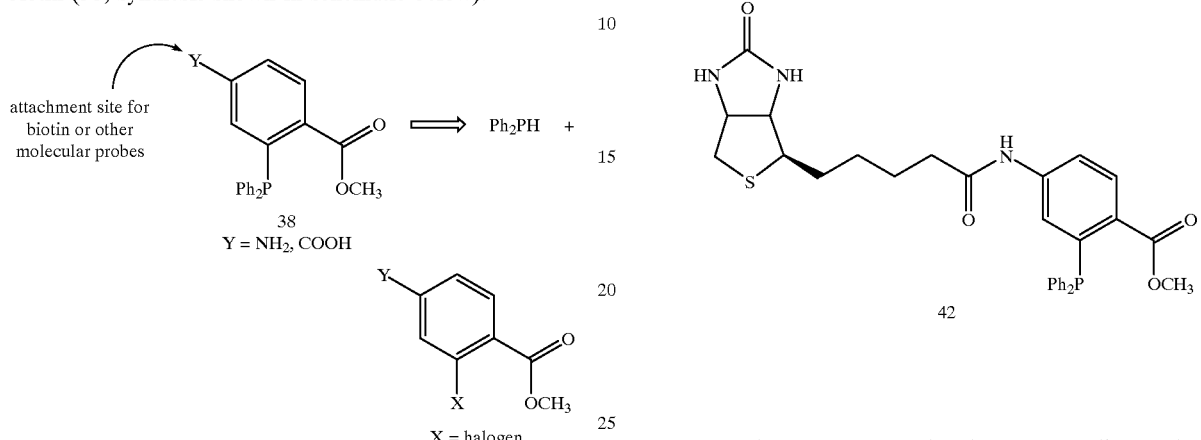

Two different routes to such a compound were investigated, the first is shown in Scheme 12.

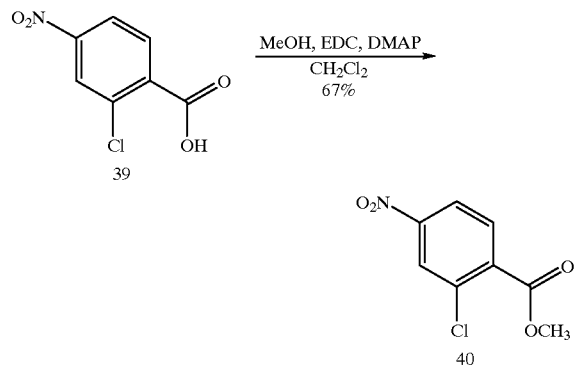

Compound 39 was converted to the corresponding methyl ester 40. The synthesis of 40 was carried out with the intention of displacing the chloride with lithium diphenylphosphide to produce phosphine 41 (Stelzer et al. *J. Organomet. Chem.* 1996, 522, 69). Reduction of 41 to an aromatic amine, followed by coupling with biotin would yield 42. However no phosphine product was isolated in the reaction either with 40 or its precursor 39.

In a second route (Scheme 13), compound 43 was converted to 44 by diazotization followed by iodide displacement. Reaction of 44 with diphenylphosphine, mediated by Pd, produced 45. Compound 45 is a key intermediate since the two carboxylic acid functionalities are selectively protected such that one can act as the aza-ylide trap and the other as a linker to the biotin label. Coupling to commercially available biotin-LC-PEO-amine (46) provided the final product 47 in which the tetraethyleneglycol linker is incorporated to enhance water solubility of the phosphine.

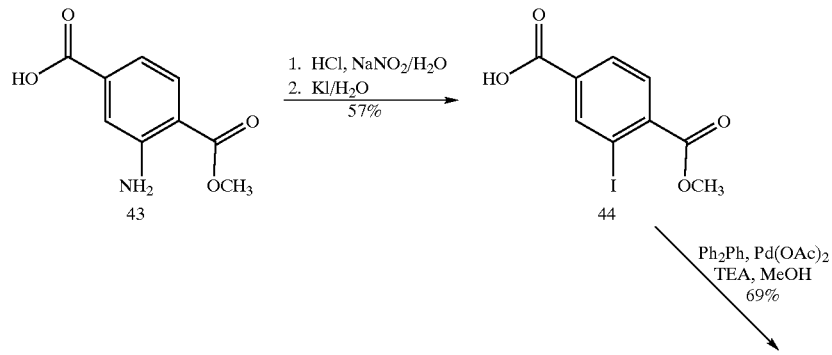

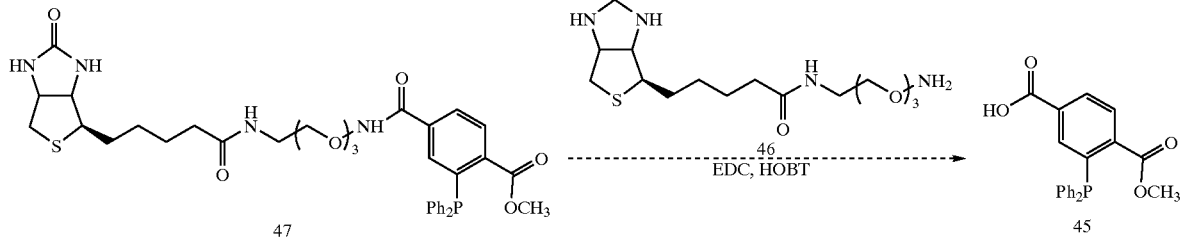

Figure 4:
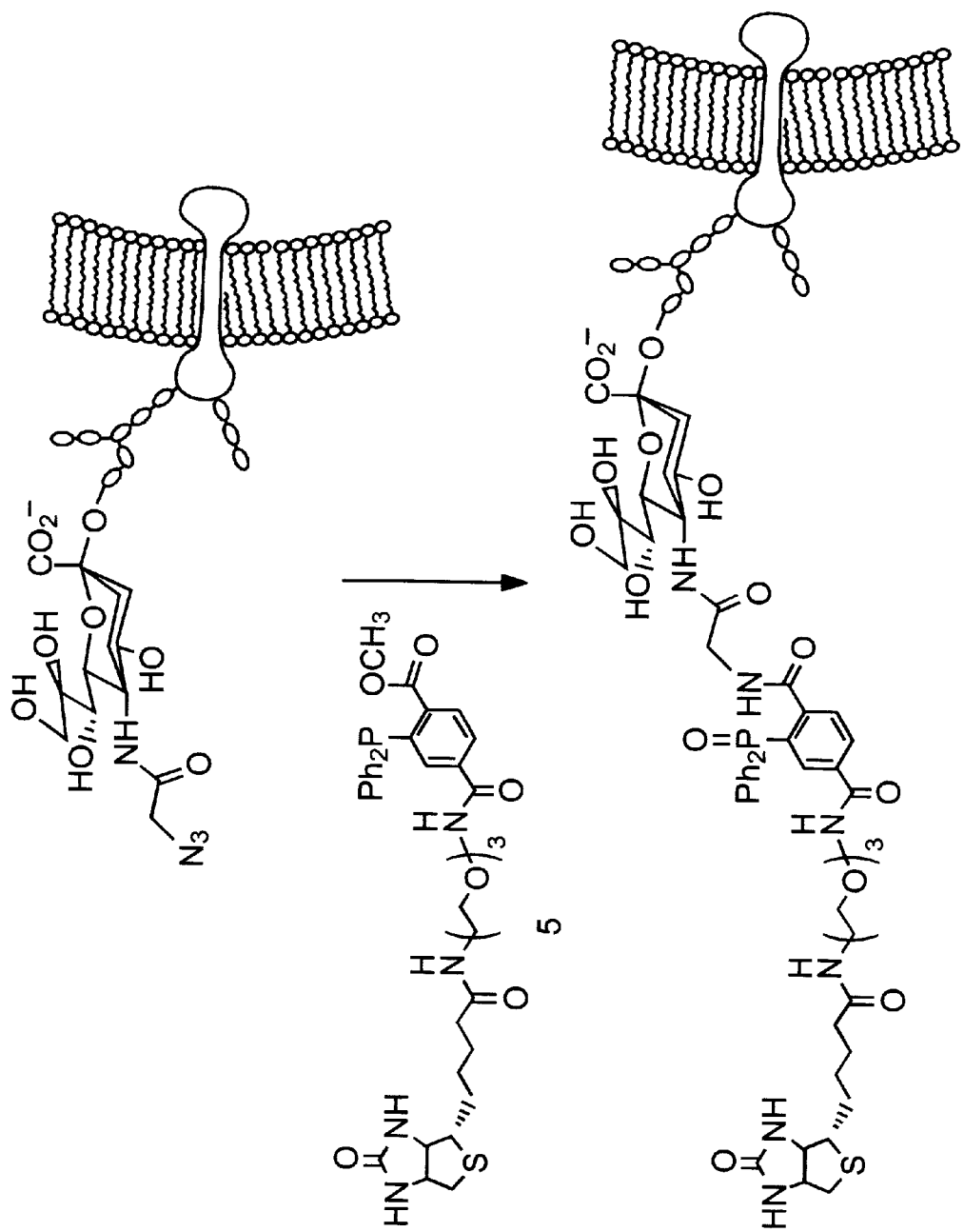
FIG. 4 a schematic illustrating reaction of biotinylated phosphine with cell surface azido sialic acid generated by metabolism of acetylated N-azidoacetylmannosamine.

The above reaction provided 39% yield of 47. Reaction of 47 with cell surface azido-sialic acid is illustrated in FIG. 4.

Expression of Azide on Cell Surfaces

Figure 5:
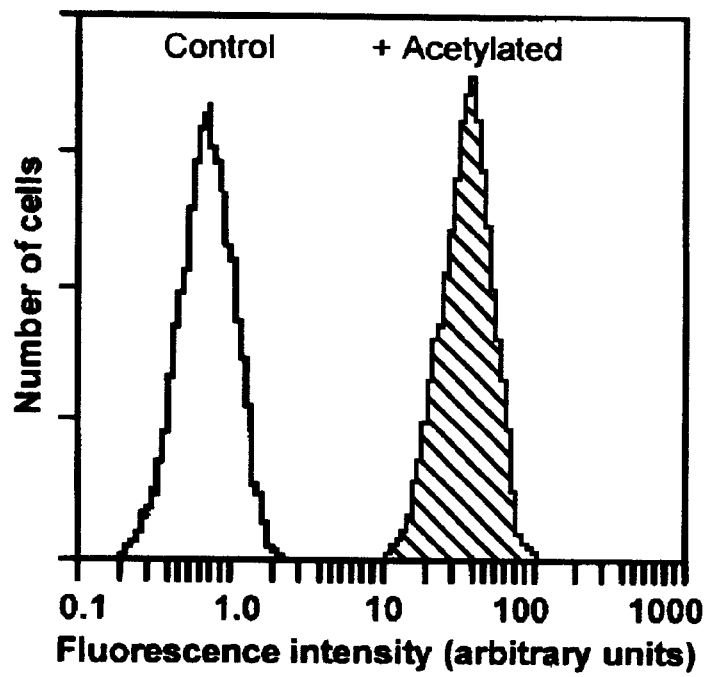
FIG. 5 is a graph showing the flow cytometry analysis of cells cultured in the presence (+acetylated) or absence (control) of N-azidoacetylmannosamine and then reacted with biotinylated phosphine reactant according to the invention.

To test the uptake and surface expression of azides on cells, Jurkat cells ($1.25 \times 10^5$) were cultured in the presence or absence (control) of N-azidoacetylmannosamine, in acetylated form at a concentration of 20 μM for 3 days. The cells were washed twice with 1 ml buffer (0.1% FBS in PBS, pH 7.4) and diluted to a volume of 240 μl. Samples were added to 60 μl of a solution of compound 47 (1 mM in PBS, pH 7.4) and incubated at room temperature for 1 hr. The cells were washed and resuspendened in 100 μl of buffer, then added to 100 μl of FITC-avidin staining solution (1:250 dilution in PBS). After a 10 min incubation in the dark at 4° C., the cells were washed with 1 ml buffer and the FITC-avidin staining process repeated. The cells were washed twice with buffer, then diluted to a volume of 300 μl for flow cytometry analysis (FIG. 5). Jurkat cells treated with acetylated 20 (compound 36) showed a dramatic increase in fluorescence which indicated the accumulation of biotin moieties on the cell surface, whereas untreated cells showed only a background level of fluorescence after exposure to phosphine 45. Similar results were obtained in two replicate experiments.

HeLa cells responded similarly to incubation with acetylated 20 (36) followed by reaction with compound 45. Notably, HeLa cells that were cultured for an additional 3 days after the modified Staudinger reaction showed no change in growth rate. Thus, neither metabolism of azidosugars, reaction with phosphine 45, nor the covalent attachment of phosphine oxide adducts to the cell surface appeared to affect cell viability.

The magnitude of the fluorescence signal was dependent upon the concentration of phosphine 45 and the reaction time and on the dose of the azidosugar. Furthermore, the fluorescence signal was reduced by the addition of tunicamycin during incubation of Jurkat cells with the azidosugar, in agreement with previous observations that most sialic acids on Jurkat cells reside within N-linked glycans (Yarema et al. *J. Biol. Chem.* 1998, 273, 31168). The background fluorescence was identical to that observed with Jurkat cells that were not exposed to any reagents and thus represents autofluorescence of cells and not non-specific uptake of the biotin probe or FITC-avidin.

Correlation of Fluorescent Intensity and Number of Azide Moieties on the Cell Surface Using biotinylated beads of known biotin density, we were able to correlate the fluorescence intensities observed by flow cytometry with the number of dye molecules on a particle or cell (Mahal et al. *Science* 1997, 276, 1125). On this basis, we determined that Jurkat cells treated with 40 mM acetylated 20 for 3 days, followed by reaction with 1 mM compound 47 for 1 hour, accumulated approximately 850,000 biotin moieties on the cell surface. This value places a lower limit on the number of azides present on the cell surface, as some azides may be concealed within the glycocalyx and therefore not accessible to the phosphine reagent. Furthermore, the cell surface reaction may not proceed in quantitative yield as observed with the model reaction. Higher densities of cell surface biotin moieties could be achieved by extending the reaction time.

Figure 6:
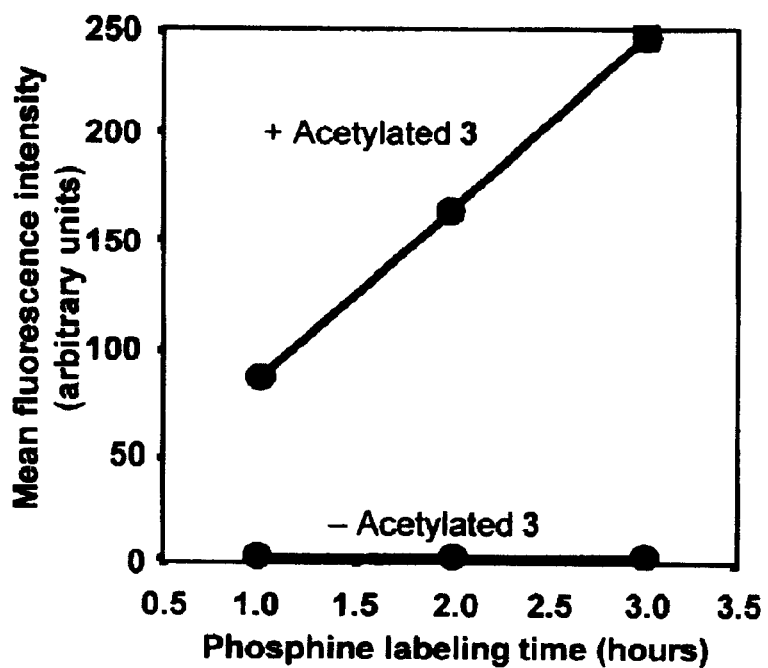
FIG. 6 is a graph showing the mean fluorescence intensity of cells cultured in the presence (+acetylated 3) or absence (control) of N-azidoacetylmannosamine, then treated with biotinylated phosphine reactant according to the invention for the time indicated.
Figure 7:
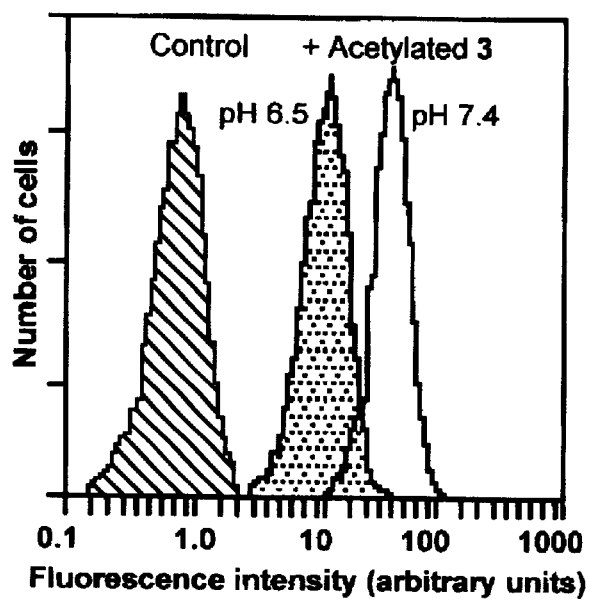
FIG. 7 is a graph showing the mean fluorescence intensity of cells cultured in the presence (+acetylated 3) or absence (control) of N-azidoacetylmannosamine, then treated with biotinylated phosphine reactant according to the invention under different conditions of pH.

Increasing the concentrations of the azidosugar or phosphine probe also elevated the level of cell surface modification. For example, Jurkat cells treated with 40 mM acetylated 20 for 3 days, followed by reaction with 2 mM compound 47 for 3 hours, accumulated approximately 4.5 million biotin moieties on the cell surface. The cell surface reaction yield was observed to be dependent upon pH; reaction at pH 6.5 produced 75% of the fluorescence signal observed at pH 7.4. Higher densities of cell surface biotin moieties could be achieved by extending the reaction time as shown in FIG. 6. Increasing the concentrations of the azidosugar or phosphine probe also elevated the level of cell surface modification. For example, Jurkat cells treated with 40 μM acetylated 3 for 3 days, followed by reaction with 2 mM compound 5 for 3 hours, accumulated approximately 4.5 million biotin moieties on the cell surface. We observed a dependence of the cell surface reaction yield on pH; reaction at pH 6.5 produced 75% of the fluorescence signal observed at pH 7.4 (FIG. 7). This is consistent with previous observations that protonation of aza-ylides facilitates their hydrolysis, a competing side reaction of the modified Staudinger process (Golobov et al. *Tetrahedron* 1992, 48, 1353.)

Figure 8:
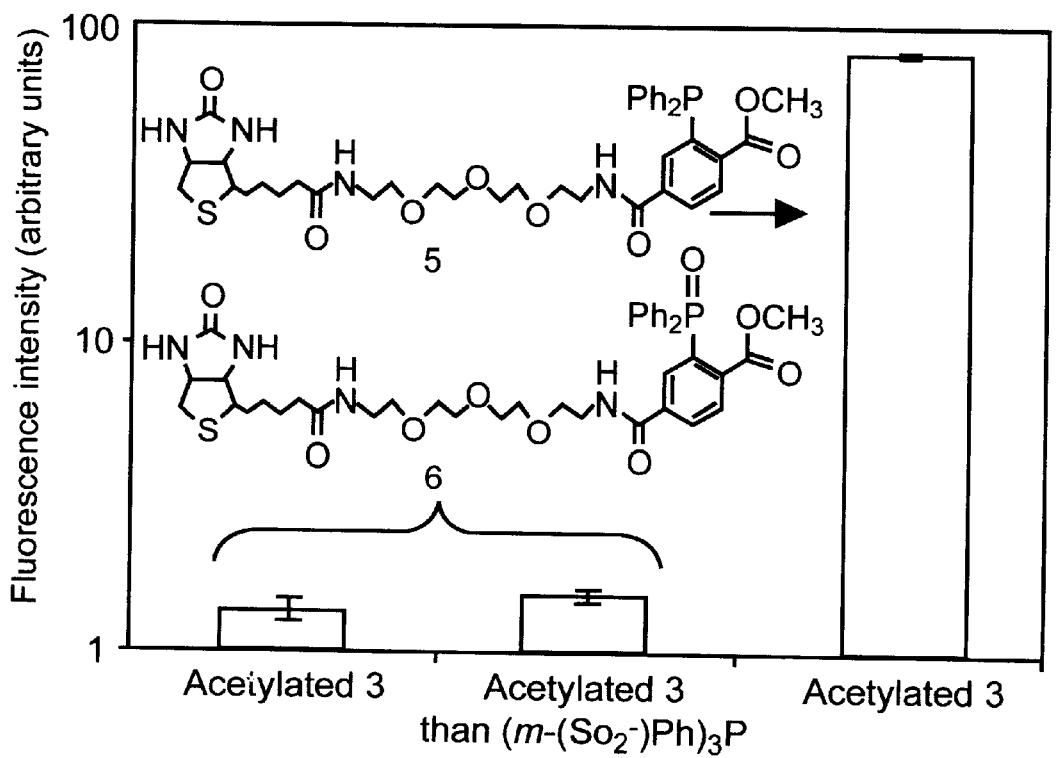
FIG. 8 is a graph illustrating the relative fluorescence intensity of cells treated with N-azidoacetylmannosamine and either reduced intentionally with a trisulfonated triphenylphosphine or left unreduced. Phosphine oxide, the product of the classical Staudinger reaction, was prepared independently and incubated with the cells. This experiment shows that cell surface biotinylation does not proceed via classical Staudinger azide reduction followed by non-specific acylation. Error bars represent the standard deviation of two replicate experiments.

Cell Surface Biotinylation Does Not Proceed via Classical Staudinger Azide Reduction Followed by Non-Specific Acylation A possible alternative explanation for the azide-dependent localization of biotin on cells might be that phosphine 47 reduced cell surface azides to the corresponding amines via the classical Staudinger reaction, simultaneously producing phosphine oxide, which in turn might non-specifically acylate cell-surface amines. If so, the reaction would lose the critical element of selectivity sought for biological applications. To address this possibility, phosphine oxide was independently synthesized and its reactivity with cells tested (1 mM for 1 hr). Two populations of Jurkat cells were pretreated with the azidosugar to engender cell surface azides as described above. One population was then further reacted with a water-soluble trisulfonated triphenylphosphine to intentionally reduce the azides. In both cases, no cell-surface biotinylation was observed. This result contrasts markedly with the extensive biotinylation of azidosugar-treated cells reacted with phosphine 47 (FIG. 8). Therefore, the chemoselective ligation reaction proceeds as designed without complications arising from nonspecific amine acylation.

Triarylphosphines Do Not Reduce Disulfide Bonds at the Cell Surface

Figure 9:
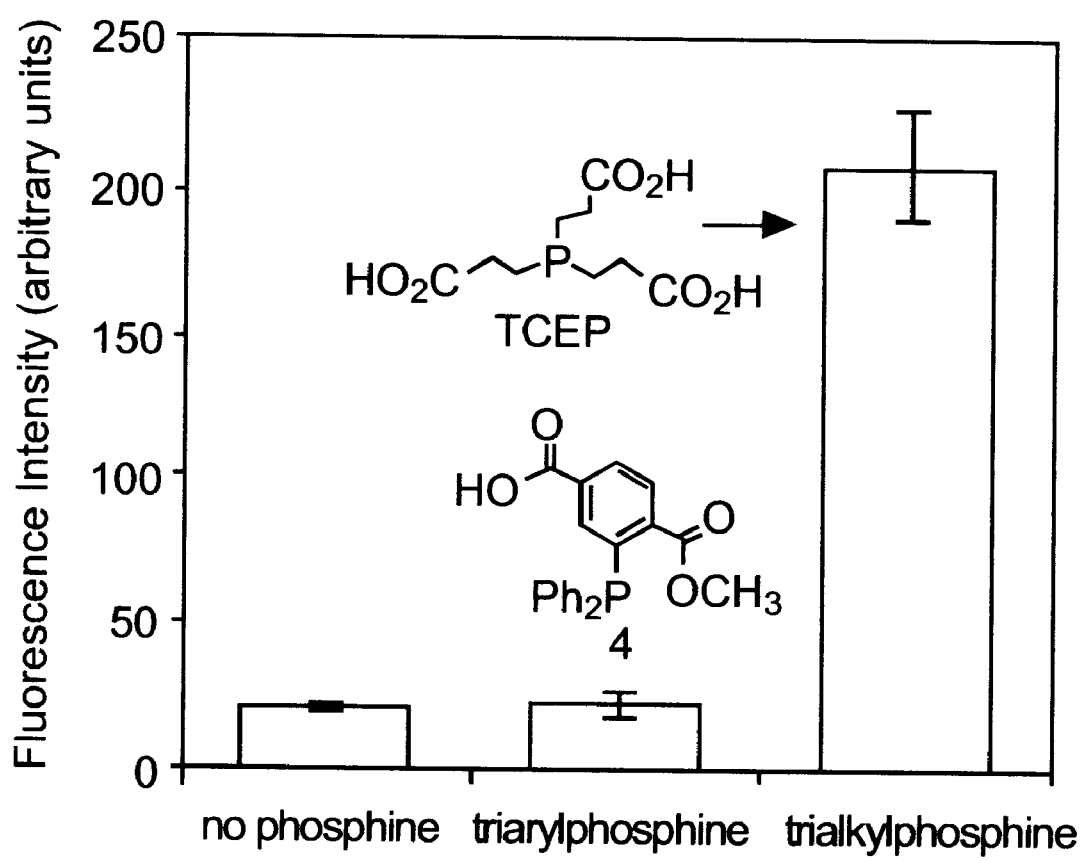
FIG. 9 is a graph showing the relative fluorescence intensity of samples prepared from cells incubated with no phosphine, triaryl phosphine or TCEP, and then combined with iodoacetylbiotin. These data show that triarylphosphines do not reduce disulfide bonds at the cell surface. Error bars represent the standard deviation of two replicate experiments.

To satisfy the requirement of chemical orthogonality, both participants in the reaction may not engage functional groups endogenous to cells. Triarylphosphines are mild reducing agents, which raises the possibility of disulfide bond reduction as an undesirable side reaction. We addressed this issue by incubating Jurkat cells with triarylphosphine, an intermediate in the synthesis of 47, and quantifying the appearance of free sulfhydryl groups on the cell surface with iodoacetylbiotin and FITC-avidin (FIG. 9). Following incubation, cells were pelleted washed with PBS, and diluted to a volume of 240 μl. Samples were combined with 60 μl of a solution of iodoacetylbiotin (5 mM in PBS). After incubation in the dark at room temperature for 1.5 hrs, the cells were washed with buffer, stained with FITC-avidin, and analyzed by flow cytometry.

After 1 hour in the presence of 1 mM triarylphosphine, no detectable increase in free sulfhydryl groups was observed relative to cells exposed to iodoacetylbiotin alone (FIG. 9). In a positive control experiment, Jurkat cells were incubated with the trialkylphosphine TCEP (1 mM, 1 hour, room temperature), a commercial disulfide bond reducing agent. A dramatic increase in free cell-surface sulfhydryl groups was observed in this case. Therefore, triarylphosphines are essentially unreactive toward disulfide bonds under these conditions, rendering ligation with azides the predominant pathway for reactivity.

Conclusions

In a side-by-side comparison with previously reported cell surface ketone reaction, (Mahal et al. *Science* 1997, 276, 1125), the cell surface Staudinger process of the invention is superior in several respects. For example, using the same reagent concentrations, azidosugar metabolism followed by phosphine reaction produced two-fold higher fluorescence than ketosugar metabolism followed by hydrazide reaction. This may reflect either a faster reaction at the cell surface, or more efficient metabolism of azidosugar 20 as compared to the ketosugar. The azide has a major advantage over the ketone in that its reactivity is unique in a cellular context due its abiotic nature. Ketones, by contrast, abound inside cells in the form of metabolites such as pyruvic acid and oxaloacetate. It should be noted that the modified Staudinger reaction is chemically orthogonal to ketone ligations and should allow tandem modification of cell surfaces with the two chemistries.

EXAMPLE 7

Application of the Staudinger Ligation to Native Chemical Ligation of Peptides—Synthesis of Peptide with C-Terminal Methyl Phosphine and Peptide with N-Terminal Azide The chemoselective ligation reaction scheme of the invention can also be applied to native chemical ligation of peptides to generate large proteins. In contrast to the application of the invention describe above provide a covalent linkage between two reactants, this application provides a slight adaptation which allows for transfer of one of the phosphine substituents to an azido-compound. Rather than forming a product with the two reactants covalently bound, the oxidized phosphine is released as a byproduct. This reaction is well suited for use in forming a peptide bond (Scheme 14).

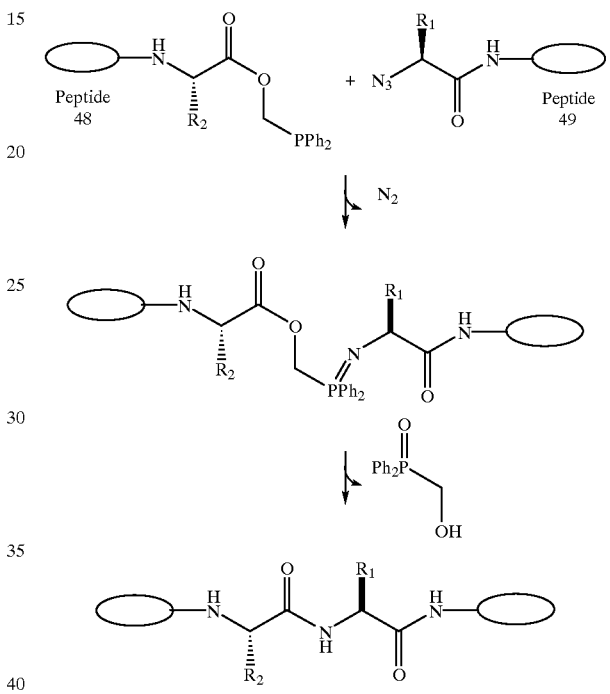

Scheme 14

The two components required are a peptide bearing a C-terminal methylphosphine ester (48) and a peptide bearing an N-terminal α-azido acid (49, Scheme 14). α-Azido acids (50) are accessible from the corresponding α-bromo acids (51) which can be synthesized in high yield from the protected α-amino acids (52, Scheme 15) (Souers et al. *Synthesis-Stuttgart* 1999, 583). These α-azido acids can be incorporated at the N-terminus of a peptide via standard solid phase peptide synthesis.

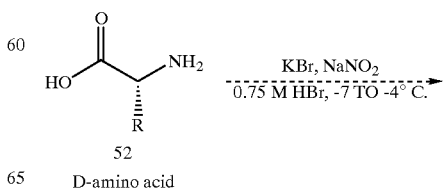

Scheme 15

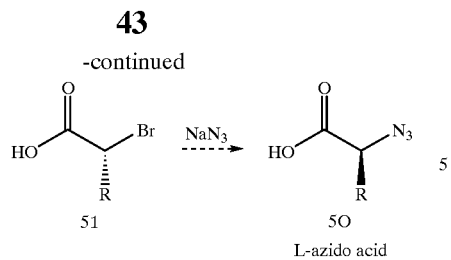

51　　　　　　　　50
　　　　　　L-azido acid

Methylphosphine amino acid esters have not been reported. One possible synthetic route is based on phosphine 53 (Slany et al. *Tetrahedron Lett.* 1996, 37, 9053), which was synthesized in high yield from diphenylphosphine (14) and paraformaldehyde (54, Scheme 16). Coupling of 53 to Fmoc-protected alanine to produce the phosphine-amino acid 55.

Scheme 16

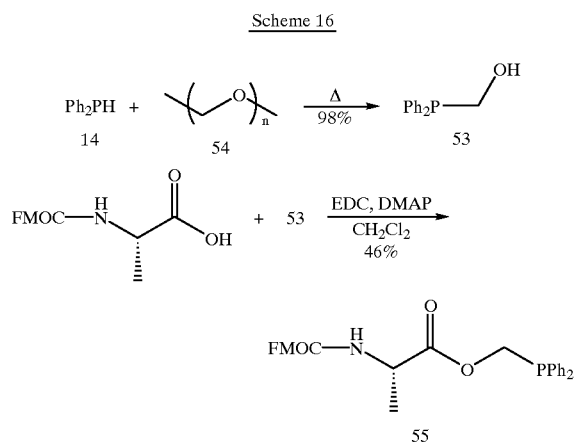

Prior to further investigation of 55, the acetylated analog 56 (Scheme 17, FIG. 12) was synthesized from 53 and used as a model methylphosphine ester. Compound 56 was exposed to methyl azidoacetate (57) with the hope of generating amide 58.

Both anhydrous and aqueous conditions were studied but only azide reduction to the amine was observed, without the desired acetate transfer. It is possible that the conformation of the aza-ylide (59) that is required for acetate transfer is sufficiently high in energy that hydrolysis becomes the favored reaction pathway. A proposed solution is to increase the rigidity of the linkage between the phosphine and the ester, as in 60 in Scheme 18, for the desired transfer to take place.

Scheme 18

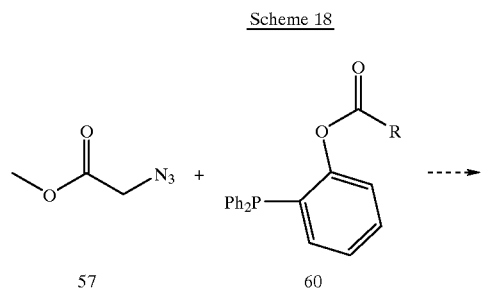

57　　　　　　60

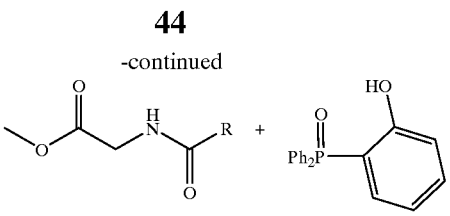

After establishing an optimal linker for acyl transfer, the scope of the reaction is determined using a series of unprotected amino acid phosphine esters. This reaction should have fewer restrictions than current methods with regard to the amino acids present at the site of ligation. Adaptation to solid phase will be the final step in developing a new native chemical ligation reaction and thereby extending the applicability of this method.

EXAMPLE 8

Incorporation of Unnatural Amino Acids Containing Azides into Recombinant Proteins Expressed in *E. Coli*

Unnatural amino acids containing azides are incorporated into recombinant proteins expressed in *E. coli* via the method described in Kiick K L, Tirrell D A. *Tetrahedron* 2000. 56: 9487. These azide containing proteins are then selectively reacted with a phosphine reagent.

In a first example of this technique, involves a phosphine having a peptide antigen that can be detected with an antibody after attachment to the recombinant protein. Two azide containing amino acids have been tested for incorporation by *E. coli*, azidoalanine and homoazidoalanine. The synthesis of these two compounds is described below. Amino acids of the general type "i" illustrated in the structures below can be used, with two other specific examples shown as well:

D or L amino acid

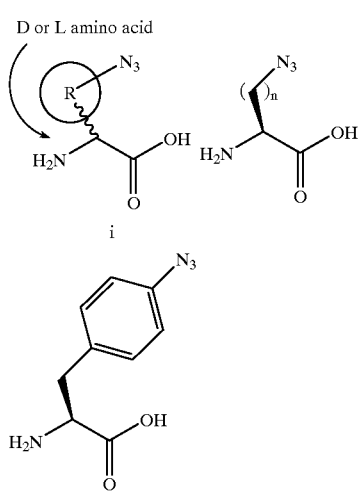

i

The phosphine probe that was used was similar to the biotin phosphine used earlier for cell surface engineering as described above. Compound 45 was added to a FLAG peptide synthesized on solid phase. The reaction is illustrated below:

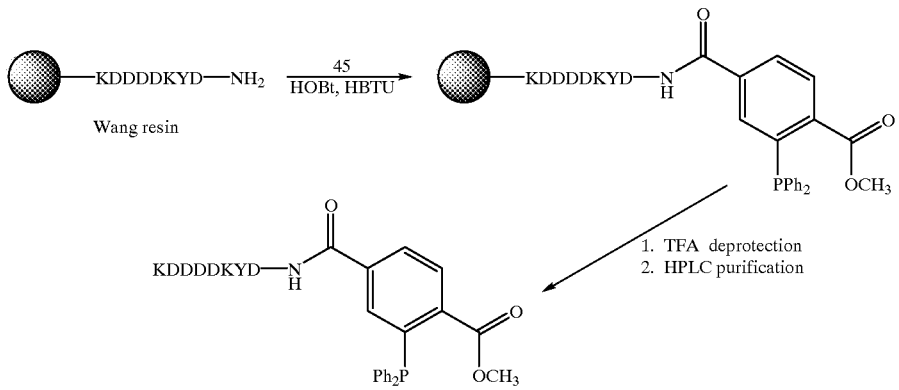

Phosphines of this type can be used to modify recombinant proteins comprising azide and also synthetic or semi-synthetic proteins that are not subject to the same restrictions on size of the unnatural amino acid. The synthesis of azidoalanine and homoazidoalanine are described in more detail below.

Synthesis of Azidoalanine

Figure 10:
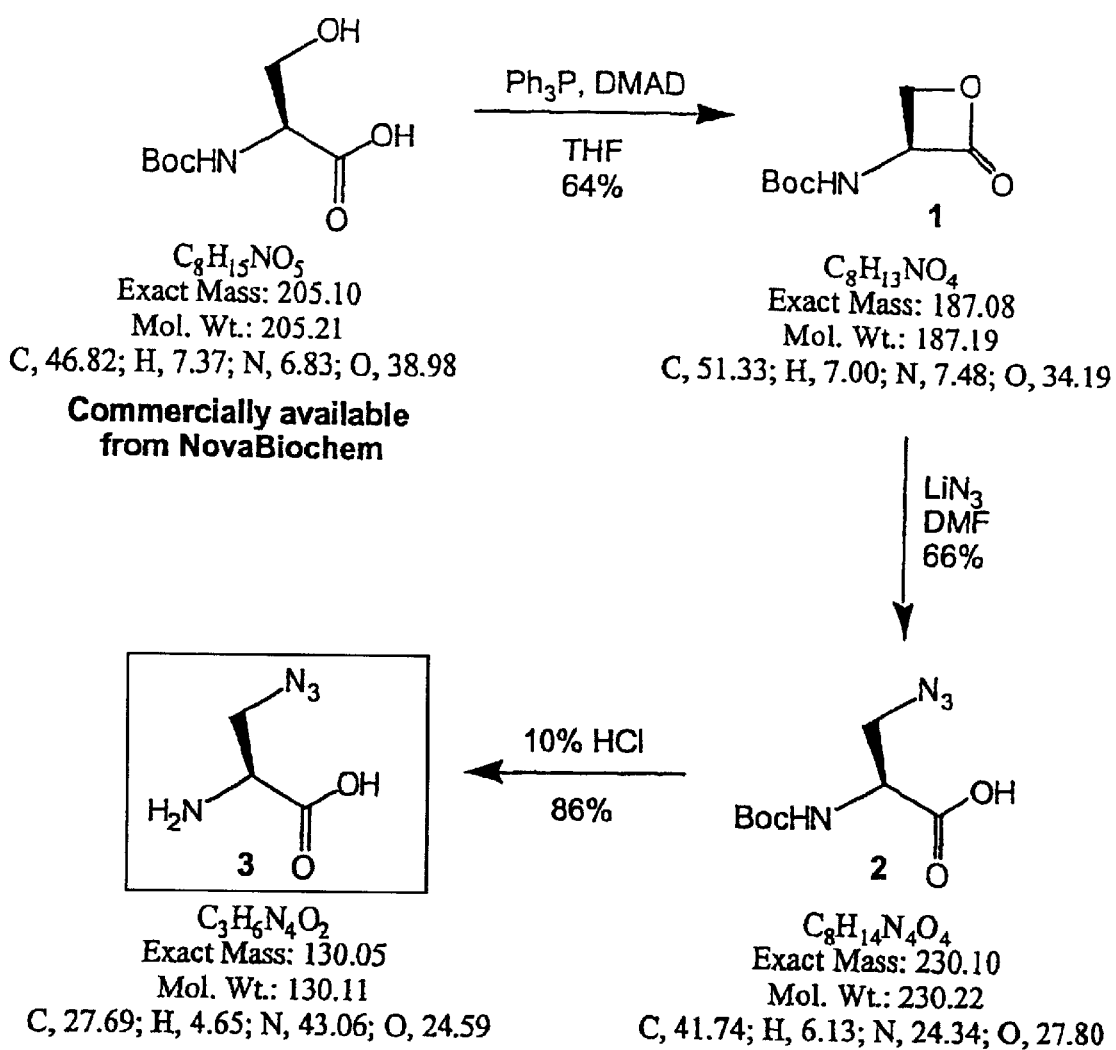
FIG. 10 is a schematic showing synthesis of azidoalanine.

The overall route of synthesis of azidoalanine is shown in FIG. 10, with experimental details provided below.

Compound 1 of FIG. 10

All solids were dried for 24 h over $P_2O_5$ before use. THF was freshly distilled. Triphenylphosphine (1.3 g, 4.9 mmol) was dissolved in 20 mL THF and cooled to −78° C. While stirring, Dimethylazodicarboxylate (0.71 g, 4.9 mmol) was added dropwise via syringe over a period of 10 min and then stirred for an additional 10 min. A solution of BocSerOH (1.0 g, 4.9 mmol) in 20 mL THF was added slowly via syringe. The reaction mixture was stirred for 4 hours while being allowed to come to room temperature. Product has an Rf of ~0.85 in 1:1 hexane:ethyl acetate. Bromocresol green was used to visualize the product. Solvent was removed via rotary evaporation. Column chromatography (20:1 to 5:1 hexane:ethyl acetate) yielded 586 mg (64%) of compound 1.

Compound 2 of FIG. 10

Compound 1 of FIG. 10 (970 mg, 5.2 mmol) was dissolved in 6 mL DMF and $LiN_3$ (278 mg, 5.7 mmol) was added. The reaction mixture was stirred overnight at room temperature. Product has an Rf of ~0.20 in 4:1 chloroform:methanol. Ninhydrin was used to visualize the product. The solvent was removed and the residue was chromatographed in 20:1 chloroform:methanol to provide 789 mg (66%) of compound 2 of FIG. 10.

Compound 3

Compound 2 of FIG. 10 (789 mg, 3.4 mmol) was dissolved in 10% HCl at 0° C. The reaction was stirred overnight while being allowed to reach room temperature. Product has an Rf of ~0.45 in 48:48:2:2 chloroform:methanol:water:acetic acid. Ninhydrin was used to visualize the product. The solvent was removed and the product was chromatographed in this same solvent to yield 382 mg (86%) of compound 2 of FIG. 10.

Synthesis of Homoazidoalanine

Figure 11:
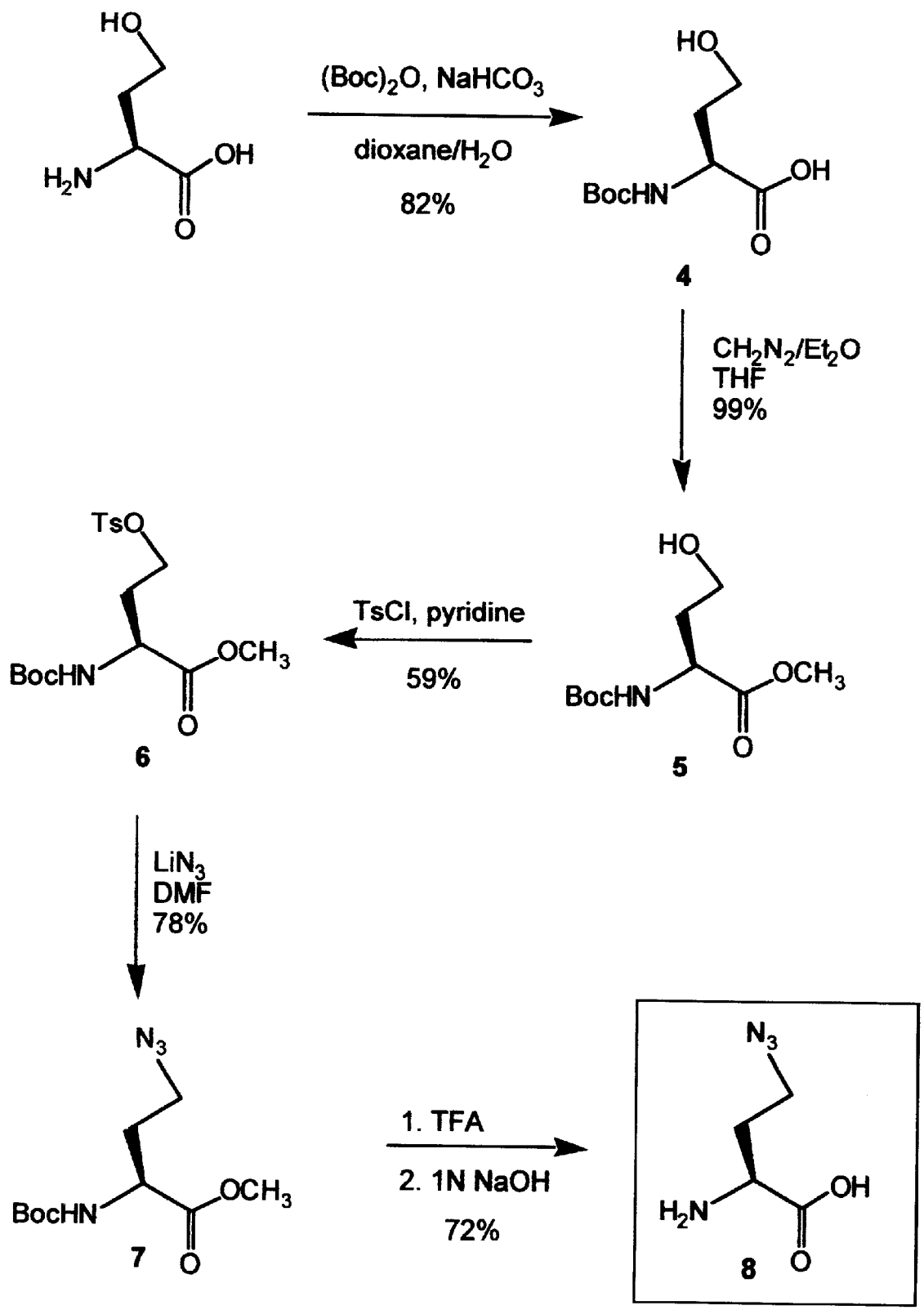
FIG. 11 is a schematic showing synthesis of homoazidoalanine.

The overall route of synthesis of homoazidoalanine is shown in FIG. 11, with experimental details provided below.

Compound 4 of FIG. 11

Homoserine (2.5 g, 20.9 mmol) was dissolved in 37 mL dioxane and 35 mL $H_2O$. The reaction mixture was cooled to 0° C. and NaHCO3 (4.39 g, 52.3 mmol) was added. A solution of Boc anhydride (5.49 g, 25.2 mmol) in 12 mL dioxane was added dropwise via syringe. The reaction was allowed to warm up to room temperature while stirring overnight. Solvent was removed by rotary evaporation and the residue was dissolved in 50 mL $H_2O$. This solution was washed with ether and then acidified to pH 2 with 5% aq. $KHSO_4$. This solution was extracted with ethyl acetate and the organic layer was dried over $Na_2SO_4$. The solvent was removed to provide 4 (3.74 g, 82%).

Compound 5 of FIG. 11

The product from the above reaction was dissolved in 75 mL THF and an ethereal solution of diazomethane was added dropwise with vigorous stirring until yellow color remained. Acetic acid was then added dropwise until the solution was colorless. Evaporation of solvent provided 5 (3.8 g, 99%).

Compound 6 of FIG. 11

Compound 5 of FIG. 11 (3.8 g, 16.3 mmol) was dissolved in distilled pyridine (18 mL) and cooled to 0° C. Tosyl chloride (3.73 g, 19.6 mmol) was added as a solid. The reaction was stirred over night while coming to room temperature. Ether (50 mL) was added and the organic layer was washed with cold 1N HCl, followed by sat. NaCl and then dried over $Na_2SO_4$. Solvent was removed and the crude product was purified by silica gel chromatography with a gradient of 10:1 to 2:1 hexanes:ethyl acetate. This provided 6 (3.7 g, 59%).

Compound 7 of FIG. 11

Compound 6 of FIG. 11 (3.6 g, 9.3 mmol) was dissolved in 30 mL DMF and $LiN_3$ (548 mg, 11.2 mmol) was added as a solid. The reaction was stirred overnight at room temperature and then poured into 120 mL $CH_2Cl_2$. The organic layer was washed with cold 1N HCl, then sat. NaCl, dried and the solvent was removed. The crude product was purified by silica gel chromatography (10:1 hexanes:ethyl acetate) to yield 7 (1.86 g, 78%).

Compound 8 of FIG. 11

The final product was obtained in a two stage deprotection by first treating with 10 mL TFA and stirring at rt for 10 min. The solvent was removed and the residue was dissolved in $H_2O$ and lyophilized. The dry crude product was dissolved in 1N NaOH (10 mL) and stirred for 3 h. The solution was brought to pH 1 with 1N HCl and then applied to Dowex-50-H+resin. The resin was washed with water and then the product was eluted with 0.3M $NH4^+OH^-$. Lyophilization afforded 8 (0.74 g, 72%).

Results

Homoazidoalanine was successfully incorporated into polypeptides using the methods of Kiick et al., 2000 supra. Attempts to incorporate azidoalanine have not been successful to date.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A compound of the formula:

$$Y\text{-}Z\text{-}PR_2R_3$$

where

Z is an aryl group substituted with $R_1$, wherein $R_1$ is in the ortho position on the aryl ring relative to the $PR_2R_3$; and wherein $R_1$ is an electrophilic group;

$R_2$ and $R_3$ are independently aryl groups, substituted aryl groups, or cycloalkyl groups; and Y is a reactive group selected from the group consisting of a carboxyl, an amine, an ester, a thioester, a sulfonyl halide, an alcohol, a thiol, a succinimidyl ester, an isothiocyanate, an iodoacetamide, a maleimide, and a hydrazine.

2. The compound of claim 1, wherein $R_1$ is selected from the group consisting of a carboxylic acid, an alkyl ester, an aryl ester, a substituted aryl ester, an aldehyde, an amide, an aryl amide, an alkyl halide, a thioester, a sulfonyl ester, an alkyl ketone, an aryl ketone, a substituted aryl ketone, a halosulfonyl, a nitrile, and a nitro.

3. The compound of claim 1, wherein $R_1$ is a lower alkyl ester.

4. The compound of claim 3, wherein the lower alkyl ester is a methyl ester.

* * * * *

UNITED STATES PATENT AND TRADEMARK OFFICE
CERTIFICATE OF CORRECTION

PATENT NO. : 6,570,040 B2
APPLICATION NO. : 09/810864
DATED : May 27, 2003
INVENTOR(S) : Eliana Saxon et al.

Page 1 of 1

It is certified that error appears in the above-identified patent and that said Letters Patent is hereby corrected as shown below:

Column 1, line 10:

Please replace the Statement as to Federally Sponsored Research with the following:

STATEMENT AS TO FEDERALLY SPONSORED RESEARCH
"This invention was made, at least in part, with a government grant from the National Institutes of Health (Grant Nos. NIH grant GM58867-01), the Office of Naval Research (Grant No. N00014-98-0605), and the Department of Energy (Order No. N00014-98-F-0402, Contract No. DE-AC03-76SF00098). The U.S. government may have certain rights in this invention." to read:

STATEMENT AS TO FEDERALLY SPONSORED RESEARCH
-- This invention was made with government support under Grant No. GM58867-01 awarded by National Institutes of Health, Grant No. N00014-98-1-0605 awarded by Office of Naval Research, and Order No. N00014-98-F-0402, Contract No. DE-AC03-76SF00098 awarded by the U.S. Department of Energy. The U.S. government has certain rights in this invention. --

Signed and Sealed this

First Day of September, 2009

David J. Kappos
*Director of the United States Patent and Trademark Office*